United States Patent [19]

Kelly et al.

[11] Patent Number: 4,978,757
[45] Date of Patent: Dec. 18, 1990

[54] 1,2,8,8A-TETRAHYDROCYCLOPROPA (C) PYRROLO [3,2-E)]-INDOL-4(5H)-ONES AND RELATED COMPOUNDS

[75] Inventors: Robert C. Kelly, Ross Township; Martha A. Warpehoski, Comstock Township; Wendell Wierenga, Oshtemo, all of Mich.

[73] Assignee: The Upjohn Company, Kalamazoo, Mich.

[21] Appl. No.: 444,176

[22] Filed: Nov. 30, 1989

Related U.S. Application Data

[60] Division of Ser. No. 894,314, Aug. 7, 1987, Pat. No. 4,912,227, which is a continuation-in-part of Ser. No. 694,363, Jan. 24, 1985, abandoned, which is a continuation-in-part of Ser. No. 581,836, Feb. 21, 1984, abandoned.

[51] Int. Cl.$^5$ .......................................... C07C 487/02
[52] U.S. Cl. .................................... 548/421; 548/433
[58] Field of Search ................................ 548/421, 433

[56] References Cited

U.S. PATENT DOCUMENTS

| | | | |
|---|---|---|---|
| 4,169,888 | 10/1979 | Hanka et al. | 424/121 |
| 4,400,518 | 8/1983 | Wierenga | 548/433 |
| 4,413,132 | 11/1983 | Wierenga | 548/491 |
| 4,423,228 | 12/1983 | Wierenga | 548/421 |
| 4,423,229 | 12/1983 | Wierenga | 548/421 |
| 4,423,230 | 12/1983 | Wierenga | 548/433 |
| 4,424,365 | 1/1984 | Wierenga | 548/421 |

OTHER PUBLICATIONS

Wierenga, W., "Synthesis . . . Left Hand Segment . . . CC-1065", *J. Am. Chem. Soc.*, 103, (1981) pp. 5621-5623.

Warpehoski, M. A. et al., "Total Synthesis . . . CC-1065", *Tetrahedron Letters*, 27, No. 35, (1986), pp. 4102-4106.

Warpehoski, M. A. et al., "Regioselective . . . CC-1065", *Tetrahedron Letters*, 27, No. 24, (1986), pp. 2735-2738.

*Primary Examiner*—Mary E. Ceperley
*Attorney, Agent, or Firm*—William G. Jameson; John T. Reynolds

[57] ABSTRACT

1,2,8,8a-Tetrahydrocyclopropa[3]pyrrolo(3,2-e)indol-4(5H)-ones, and related compounds of formulas I and intermediate therefor II

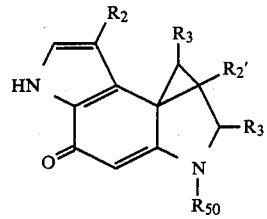

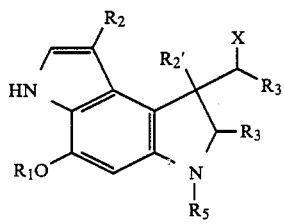

wherein
$R_2$, $R_2'$, $R_3$, $R_5$, $R_{50}$ and X are as defined in the specification, e.g., (7bR,8aS)-1,2,8,8a -tetrahydro-7-methyl-2-[[5-(((1H-indol-2-yl)carbonyl)amino)-1H-indol-2-yl]carbonyl]cyclopropa[pyrrolo[3,2-e]indol-4(5H)-one (U-71,184), as purified, and its racemic form (U-68,415), and related compounds, are useful as ultraviolet light absorbers and as antibacterials. The lead compounds are useful as antitumor drug compounds in standard laboratory animal tests.

4 Claims, No Drawings

1,2,8,8A-TETRAHYDROCYCLOPROPA (C) PYRROLO [3,2-E)]-INDOL-4(5H)-ONES AND RELATED COMPOUNDS

CROSS-REFERENCE TO RELATED APPLICATION

This application is a divisional application of U.S. Ser. No. 06/894,314, filed 7 Aug. 1987, now U.S. Pat. No. 4,912,227 which is a continuation-in-part of U.S. Ser. No. 694,363, filed 24 Jan. 1985, now abandoned, which is a continuation-in-part of U.S. Ser. No. 581,836, filed 21 Feb. 1984, now abandoned.

INTRODUCTION

This invention relates to new synthetic chemical compounds somewhat related to the antibiotic/antitumor agent CC-1065. More particularly this invention provides new compounds such as (7bR, 8aS)-1,2,8,8a-tetahydro-7-methyl-2-[[5-(((2H-indol-2-yl)carbonyl)amino)-1H-indol-2-yl]carbonyl]cyclopropa[pyrrolo[3,2-e]indol-4(5H)-one (U-71,184) as purified, and in its essentially racemic form (U-68,415), and related intermediate compounds.

BACKGROUND OF THE INVENTION

Antibiotic CC-1065 is disclosed and claimed in L. J. Hanka et al U.S. Pat. No. 4,169,888 together with a process for preparing antibiotic CC-1065 by aerobic fermentation procedures, and recovering antibiotic CC-1065 therefrom.

In *J. Am. Chem. Soc.*, 103, No. 18, 1981, W. Wierenga published a "Synthesis of the Left-Hand Segment of the Antitumor Agent CC-1065".

Wierenga U.S. Pat. No. 4,400,518 claims some new compounds of the formula

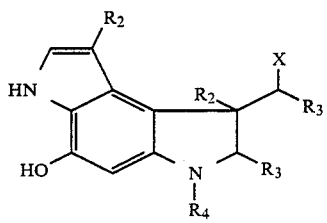

wherein
$R_2$ and $R_3$ are hydrogen, $C_1$ to $C_5$ alkyl, or phenyl;
$R_4$ is $-SO_2R_2$, $-SO_2CH_2C(O)phenyl$, $-CO_2CH_2Z$ where
Z is $-CH_2I$, $-CCl_3$, $-CH_2SO_2R_2$, phenyl or fluorenyl;
X is $-OSO_2R_2$, Cl, Br or I,
with the proviso that $R_2$ cannot be hydrogen when it is adjacent to $-SO_2$.

Wierenga U.S. Pat. No. 4,413,132 claims some compounds of the formula

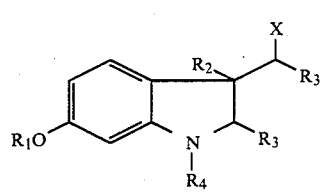

where
$R_1$ is methyl, benzyl, allyl, methylthiomethyl, methoxymethyl, methoxyethoxymethyl, 2,2,2-trichloroethyl, or $(R_2)_3$-Si-ethyl,
$R_2$ and $R_3$ are hydrogen, $C_1$ to $C_5$-alkyl, or phenyl;
$R_4$ is $-SO_2R_2$, $-SO_2CH_2C(O)phenyl$, $-CO_2CH_2Z$ where
Z is iodomethyl, trichloromethyl, $-CH_2SO_2R_2$, phenyl or fluoroenyl; and
X is $-OSO_2R_2$, chloro, bromo or iodo, with the proviso that $R_2$ cannot be hydrogen when it is adjacent to $-SO_2$.

Wierenga U.S. Pat. No. 4,423,228 claims a process for preparing an intermediate compound of the formula

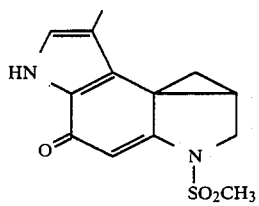

by reacting its 1-methanol pecursor with triphenylphosphine/carbon tetrahalide, and then recovering the above cyclopropa-compound from its reaction mixture.

Wierenga U.S. Pat. No. 4,423,229 claims a process for preparing a compound of the formula

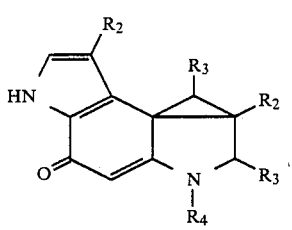

where
$R_2$ and $R_3$ are hydrogen, $C_1$ to $C_5$-alkyl or phenyl;
$R_4$ is $-SO_2R_2$, $-SO_2CH_2C(O)phenyl$ or $-CO_2CH_2Z$ where
Z is iodomethyl, trichloromethyl, $-CH_2SO_2R_2$, phenyl or fluorenyl;
by cyclizing its halomethyl or its methanesulfonate ester precursor compound.

Wierenga U.S. Pat. No. 4,423,230 claims a process for preparing a compound of the formula

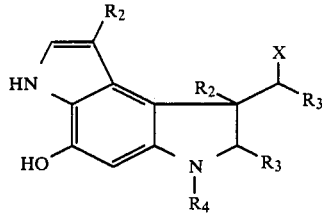

where
$R_2$ and $R_3$ are hydrogen, $C_1$ to $C_5$-alkyl, or phenyl;
$R_4$ is $-SO_2R_2$, $-SO_2CH_2C(O)phenyl$, or $-CO_2CH_2Z$ where
Z is iodomethyl, trichloromethyl, $-CH_2SO_2R_2$, phenyl or fluorenyl, and Z is —OSO₂R₂, chloro, bromo or iodo, with the proviso that R₂ cannot be hydrogen when it is adjacent to —SO₂.

Wierenga U.S. Pat. No. 4,424,365 claims compounds of the formula

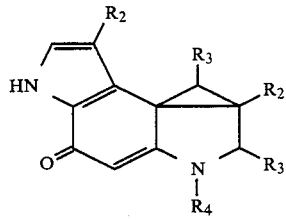

in the keto or enol form, where
R₂ and R₃ are hydrogen, C₁ to C₅-alkyl or phenyl;
R₄ is —SO₂R₂, —SO₂CH₂C(O)phenyl, or —CO₂CH₂Z where
Z is iodomethyl, trichloromethyl, —CH₂SO₂R₂, phenyl or fluorenyl.

OBJECTS OF THE INVENTION

It is an object of this invention to provide some new, synthetically obtained 1,2,8,8a-tetrahydrocyclopropa[c-]pyrrolo[3,2-e]indol-4)5H)-one derivative compounds which new compounds are useful as ultraviolet light absorbers and as antibacterials, and some of which are of interest for development as antitumor drug compounds for use as part of the therapy for treating some types of cancer in valuable animals and humans.

It is a further object of this invention to provide the art with the resolved stereo forms of selected compounds of the above type which resolved enantiomers have been found to possess the bulk of the important antitumor activity in standard laboratory animal tests.

Other objects of this invention will be apparent from the specification and the claims which follow.

SUMMARY OF THE INVENTION

This invention provides some new synthetically obtained 1,2,8,8a-tetrahydrocyclopropa[c]pyrrolo[3,2-e]indol-4(5H)-one derivative compounds of formulas I or II (see General Formulae Chart), as defined hereinafter, which are useful as light absorber substances, as antibacterial compounds, or as chemical intermediates the light absorbing or antibacterial compounds. Representative formula I compounds have also been shown to possess useful ranges of antitumor activity in standard laboratory animal tests. Two lead compounds within formula I, U-68,415 and its purified enantiomer U-71,184, have been selected for advanced testing for this antitumor drug utility. The compounds of this invention are obtained by chemical processes shown in Chart I and detailed in the examples.

DETAILED DESCRIPTION OF THE INVENTION

More specifically, this invention provides new chemical compounds of general formulae I and II (see GENERAL FORMULAE sheet) wherein R₁ in formula II is CH₃—, —CH₂Ph, CH=CHCH₂—, —CH₂SCH₃, —CH₂OCH₃, —CH₂OCH₂CH₂OCH₃, —CH₂CCl₃, —CH₂CH₂Si(R₂)₃, or H, where Ph is phenyl; R₂ is alkyl(C₁-C₅), phenyl, or H; R₂' is C₁ to C₅-alkyl, phenyl or hydrogen, and is not necessarily the same as R₂ in one compound; R₃ is alkyl(C₁-C₅), phenyl, or H; X is Cl, Br, or I-, or OSO₂R₄₀, where R₄₀ is C₁ to C₅-alkyl, phenyl, tolyl, bromophenyl, nitrophenyl, or trifluoromethyl; R₅₀ is hydrogen or the same as R₅; R₅ is a carbonyl acyl group selected from the group consisting of

  (i)

where R₆ is H, -alkyl(C1 to C₂₀), —CCl₃, CF₃, or NH₂;

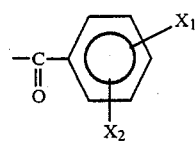  (ii)

where X₁ and/or X₂ is H, CH₃, OH, OCH₃, NO₂, NH₂, NHAc, NHBz, or halogen;

(iii) acyl derivatives

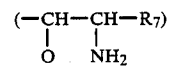

of the 20 natural amino acids where R₇ is the amino acid residue of glycine, alanine, valine, isoleucine, leucine, serine, threonine, aspartic acid, glutamic acid, lysine, arginine, asparagine, glutamine, cysteine, methionine, tryptophan, phenylalanine, tyrosine and histidine as well as proline (a ring containing acyl group formed by taking together the R₇ and —NH₂ moieties); and their common salts selected from Na⊕, K⊕, NH₄⊕, CL⊖, PO₄⊖ and OAc⊖;

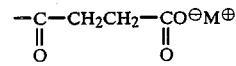  (iv)

where M⊕ is Na, K, NH₄, or N(CH₃)₄;

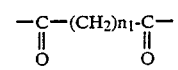  (v)

(dimer) where n₁ is 2–12;

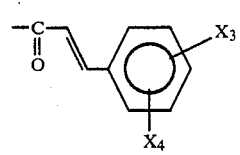  (vi)

where X₃ and/or X₄ is H, OH, or OCH₃;

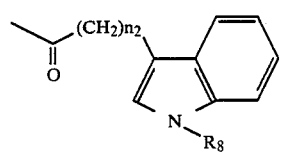  (vii)

where n₂ is 0–3; and R₈ is H, CH₃ or C₂H₅;

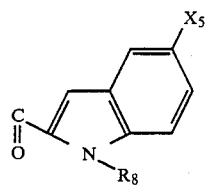

where X₅ is H, OH, OCH₃, NO₂, NH₂, NHAc,

NHBz; or NH—CN; and $R_8$ has the meaning defined above;

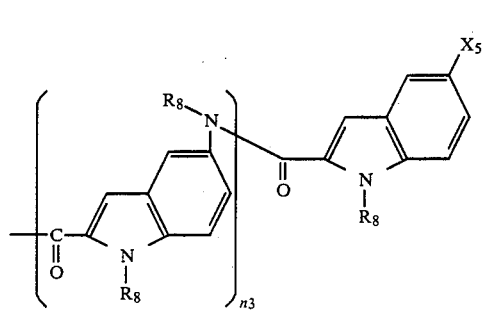

where $n_3$ is 1 to 3; and $R_8$ and $R_5$ have the meanings defined above;

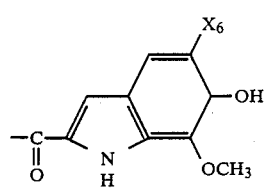

where $X_6$ is H, NO₂, NH₂, NHAc, and

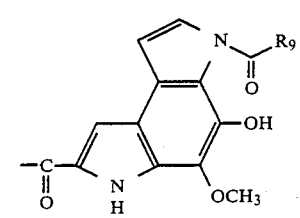

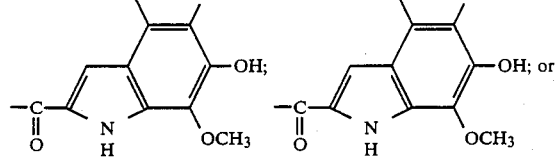

wherein $R_9$ is CH₃ or NH₂;

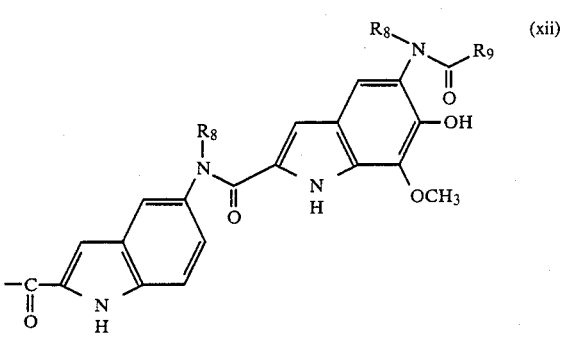

where $R_8$ and $R_9$ have the meanings defined above;

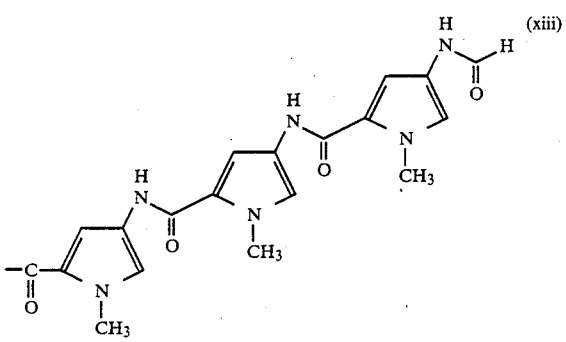

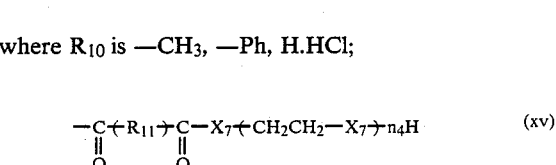

where $R_{10}$ is —CH₃, —Ph, H.HCl;

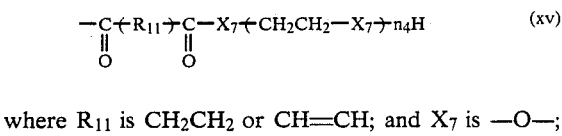

where $R_{11}$ is CH₂CH₂ or CH=CH; and $X_7$ is —O—; NH; $n_4$ is 1-4; and the HCl and MeI salts when $X_7$ is NH;

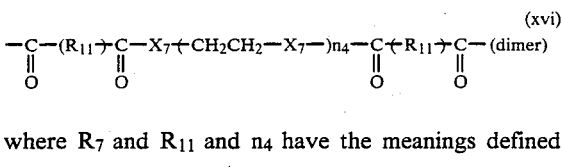

where $R_7$ and $R_{11}$ and $n_4$ have the meanings defined above;

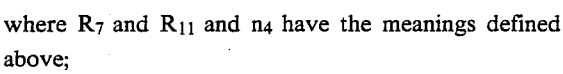

where $X_8$ is —O—, —S—, NH; $X_9$ is —CH= or —N=; and $X_5$ has the meaning defined above;

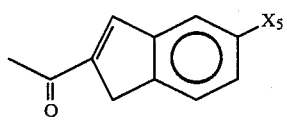 (xviii)

where $X_5$ has the meaning defined above;

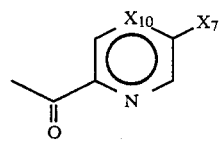 (xix)

where $X_{10}$ is —CH= or —N= and $X_7$ is SH, NH$_2$, OH, H or NHAc;

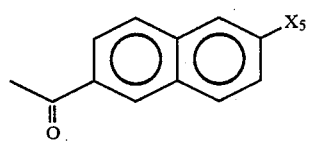 (xx)

where $X_5$ has the meaning defined above;

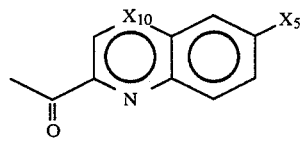 (xxi)

where $X_5$ and $X_{10}$ have the meanings defined above; and

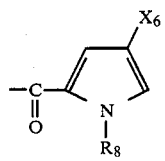 (xxii)

where $X_6$ and $R_8$ have the meanings defined above; and when any of $X_1$ to $X_6$ is OH or NH$_2$, then each of the $R_5$ groups represented above by ii, vi, viii, ix, x, xvii, xviii, xix, xx, xxi or xxii may be coupled with each other forming the following dimer combinations wherein the representative $R_5$ groups are bound together via a carboxy

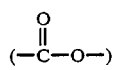

or an amide

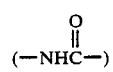

linkage;

| | |
|---|---|
| ii + ii | ix + xx |
| ii + vi | ix + xxi |
| ii + viii | ix + xxii |
| ii + ix | x + x |
| ii + xvii | x + xvii |
| ii + xviii | x + xviii |
| ii + xix | x + xix |
| ii + xx | x + xx |
| ii + xxi | x + xxi |
| ii + xxii | x + xxii |
| vi + vi | xvii + xvii |
| vi + viii | xvii + xviii |
| vi + ix | xvii + xix |
| vi + x | xvii + xx |
| vi + xvii | xvii + xxi |
| vi + xviii | xvii + xxii |
| vi + xix | xviii + xviii |
| vi + xx | xviii + xix |
| vi + xxi | xviii + xx |
| vi + xxii | xviii + xxi |
| viii + viii | xviii + xxii |
| viii + ix | xix + xix |
| viii + x | xix + xx |
| viii + xvii | xix + xxi |
| viii + xviii | xix + xxii |
| viii + xix | xx + xx |
| viii + xx | xx + xxi |
| viii + xxi | xx + xxii |
| viii + xxii | xxi + xxi |
| ix + ix | xxi + xxii |
| ix + x | xxii + xxii |
| ix + xvii | |
| ix + xviii | |
| ix + xix | |

Illustrative examples of the thus formed dimers are given below:

$R_5$ = xix + xix =

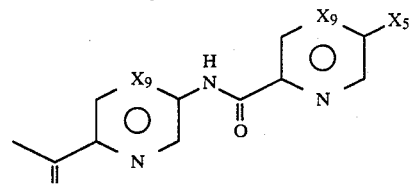

$R_5$ = xviii + viii =

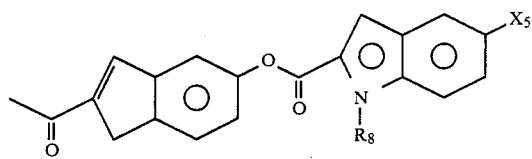

$R_5$ = ii + xxi =

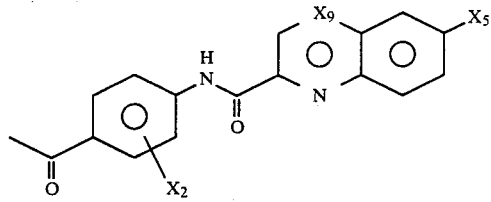

The compounds of formula (I) can be named as derivatives of the numbered ring system (A) shown on the GENERAL FORMULAE sheet. The wavy line bonds in the cyclopropa-ring of formula (A), including carbon atoms numbered 7b, 8 and 8a, are used to denote that the cyclopropa-ring can be tilted (down) toward the alpha ($\alpha$) direction or (up) beta ($\beta$) direction, relative to the plane of the ring system. An example of a specific epimer of this ring system, included in compounds of this invention can be named (7bR,8aS)-(1,2,8,8a-tetrahydro)-7-methyl-cyclopropa[c]pyrrolo[3,2-e]indol-4(5H)-one (U-71,150).

The compounds of formula II on the GENERAL FORMULA sheet can be named as derivatives of the numbering ring system (B) shown on the GENERAL FORMULAE SHEET. Such compounds will contain the 1,2,3,6-tetrahydro-3-$R_5$-8-$R_2'$-5-$R_1$-benzo[1,2-b;4,3-b']dipyrrol-1-($R_3$-CH(X))structure and X is as defined hereinabove. Examples of these Formula II compounds are described in the detailed examples hereinbelow, and the specific structures are shown in Chart I.

Examples of Formula I compounds of this invention include:

1,2,8,8a-tetrahydro-7-methyl-2-(quinolinylcarbonyl)cyclopropa[c]pyrrolo[3,2-e]indol-4(5H)-one (U-68,749);

1,2,8,8a-tetrahydro-7-methyl-2-(2-pyrrolylcarbonyl)cyclopropa[c]pyrrolo[3,2-e]indol-4(5H)-one (U-68,819);

1,2,8,8a-tetrahydro-7-methyl-2-[[5-benzoylamino-1H-indol-2-yl]carbonyl]cyclopropa[c]pyrrolo[3,2-e]indol-4(5H)-one (U-68,846);

1,2,8,8a-tetrahydro-7-methyl-2-[[5-[[5-benzoylamino-1H-indol-2-yl)carbonyl]amino]-1H-indol-2-yl]carbonyl]cyclopropa[c]pyrrolo[3,2-e]indol-4(5H)-one (U-68,880);

1,2,8,8a-tetrahydro-7-methyl-2-(1H-indol-2-ylcarbonyl)cyclopropa[c]pyrrolo[3,2-c]indol-4(5H)-one (U-66,694);

1,2,8,8a-tetrahydro-7-methyl-2-benzoylcyclopropa[c]pyrrolo[3,2-e]indol-4(5H)-one (U-66,866);

1,2,8,8a-tetrahydro-7-methyl-2-[(6-hydroxy-7-methoxy-1H-indol-2-yl)carbonyl]cyclopropa[c]pyrrolo[3,2-e]indol-4(5H)-one (U-67,785);

1,2,8,8a-tetrahydro-7-methyl-2-[[5-[[[1H-indol-2-yl]carbonyl]amino]-1H-indol-2-yl]carbonyl]cyclopropa[c]pyrrolo[3,2-e]indol-4(5H)-one (U-68,415);

(1,2,8,8a)-tetrahydro-7-methyl-2-2[[5-cyanoamino-1H-indol-2-yl]carbonyl]cyclopropa[c]pyrrolo[3,2-e]indol-4(5H)-one (U-69,058);

1,2,8,8a-tetrahydro-7-methyl-2-[[5-ureido-1H-indol-2-yl]carbonyl]cyclopropa[c]pyrrolo[3,2-e]indol-4(5H)-one (U-69,059);

1,2,8,8a-tetrahydro-7-methyl-2-[[5-[[[5-ureido-1H-indol-2-yl]carbonyl]amino]-1H-indol-2-yl]carbonyl]cyclopropa[c]pyrrolo[3,2-a]indol-4(5H)-one (U-69,060).

A compound of the above type which is being considered for advanced tumor reduction studies in the laboratory in the resolved enantiomer of U-68,415 above, (7bR, 8aS)-1,2,8,8a-tetrahydro-7-methyl-2-[[5-[[[1H-indol-2yl]carbonyl]amino-1H-indol-2-yl]carbonyl]cyclopropa[c]pyrrolo[3,2-e]indol-4(5H)-one (U-71,184).

Chart I discloses the chemical steps to make the compounds identified therein and in Chart II. The process details of each step are given in the non-limiting examples which follow. With regard to each process step, the following delineates a fuller scope of the operating details. As used herein Ac means acyl; Bn means benzyl; Bz means benzoyl; Ph means phenyl; Ms means mesyl; and Me means methyl.

Chart II—Step 1:

When $R_4$ is a sulfonamide, this N-deblocking transformation is effected by Red-Al (sodium bis-methoxyethoxy aluminum hydride) in THF/toluene or glyme [E. H. Gold and E. Babad, J. Org. Chem., 37, 2208–2210 (1972)]. This is described in detail for $R_4=SO_2CH_3$ in the following experiment.

When $R_4=SO_2CH_2COC_6H_5$, the N-deblocking can be done by Zn/HOAc/trace HCl [J. B. Hendrickson and R. Bergeron, Tet. Lett., 345 (1970)]. When $R_4=CO_2CH_2CH_2I$ the $R_4$ group can be removed by Zn/CH$_3$OH at reflux [J. Grimshaw, J. Chem. Soc., 7136 (1965)]. Similarly, Zn/aq. THF, pH 4.2, can cleave $R_4=CO_2CH_2CCl_3$ [G. Just and K. Grozinger, Synthesis, 457 (1976)]. Base (1M NaOH) cleaves $R_4=CO_2CH_2CH_2SO_2R_2$ ([G. I. Tesser and I. C. Balvert-Geers, Int. J. Pept. Protein Res., 7, 295 (1975) and A. T. Kader and C. J. M. Stirling, J. Chem. Soc., 2158 (1964)]. The benzyl carbamate ($R_4=CO_2CH_2Ph$) can be cleaved by hydrogenolysis [M. Bergmann and L. Zervas, Ber., 65, 1192 (1932)] or by one of many newer methods in the art such as TMS-I in CH$_3$CN [r. S. Lott, V. S. Chauhan and C. H. Stammer, J. Chem. Soc., Chem., Commun., 495 (1979)]. The 9-fluorenylmethyl carbamate can be cleaved by ammonia or other simple amines [M. Brodanszky, S. S. Deshame and J. Martinez, J. Org. Chem., 44, 1622 (1979)].

Step 2:

The indoline 2 can react with active acyl or sulfonyl compounds such as the chlorides or anhydrides, under conditions standard in the art (inert solvent such as ether or EtOAc; HX scavenger such as triethylamine) to effect the N-amidation. It can also be condensed with carboxylic acids in the presence of dehydrating agents such as carbodiimide. A convenient method for this approach is reaction of 2 with 1 equivalent of the carboxylic acid and 1 equivalent of EDC (ethyldimethylaminopropyl carbodiimide) in DMF [L. Grehn and U. Ragnarsson, J. Org. Chem., 46, 3492–3497 (1981)]. Alternatively, the condensation may be carried out with the commonly used dicyclohexylcarbodiimide in THF or DMF. It is not necessary to protect the alcohol functionality during this transformation.

Compounds 3 in which $R_5=$i–vii (see Chart II) can be prepared from commercially available activated acyl compounds or carboxylic acids by procedures generally known in the art. For $R_5=$viii, the acids with $X_5=$H, OH and OMe are commercially available. The 5-NO$_2$ compound is prepared by Fischer cyclization of ethylpyruvate-p-nitrophenylhydrazone in polyphosphoric acid [S. M. Parmerter, A. G. Cook and W. B. Dixon, J. Amer. Chem. Soc., 80, 4621 (1958)]. This can be converted, by procedures standard in the art, to the NH$_2$ derivative (H$_2$/PtO$_2$; Fe/HOAc) and thence to the NHAc(Ac$_2$O), NHBz (PhCOOH, EDC, DMF), and

(NaNCO) derivatives. The ureido compound can be converted to the cyanamide with MSCl in pyridine. Alkylation of the indole nitrogen can be effected by procedures in the art such as NaH/CH$_3$I or C$_2$H$_5$I.

For $R_5=$ix, the acid is prepared by DCC or EDC condensation of the acyl-protected amino indole from viii with one of the acids in that group, followed by acyl deprotection. For $R_5=$x, the acid compound wherein $X_6=$H was first prepared by R. J. S. Beer, K. Clarke, H. F. Davenport and A. Robertson [J. Chem. Soc., 2029 (1951)]. By analogy with the acids for $R_5=$viii, nitration will give the 5-$_N$O$_2$ derivative, which can be converted to the other nitrogen functional groups defined for X$_6$ as described above.

Wherein $R_5=$xi represents the phosphodiesterase inhibitors, PDE-I and PDE-II, synthesized by N. Komoto, Y. Enomoto, M. Miyagaki, Y. Tanaka, K. Nitanai and H. Umezawa [Agric. Biol. Chem., 43, 555–557 and 550–561 (1979)]. The remaining structures in this category are intermediates in an alternate synthesis of PDE-I and II. The thiomethyl compound is prepared by the Gassman reaction [P. G. Gassman, G. Gruetzmacher and T. J. Van Bergen, J. Amer. Chem. Soc., 96, 5512–5517 (1974)] between the ester of the anilinoindole-2-carboxylate described for $R_5=$x and the chlorosulfonium salt of α-thiomethyl acetaldehyde (as its acetal), with cyclization to the indole occurring after deacetalization. Raney nickel removes the thiomethyl group to yield the indole shown. Selective reduction by borane in acidic media [B. E. Maryanoff and D. F. McComsey, J. Org. Chem., 43, 2733–2735 (1978)] provides an alternate route to PDE-I and PDE-II.

For $R_5=$xii, the process used for ix is repeated on the more highly oxygenated indole derivatives listed in x, i.e., condensation of the acyl protected aniline with another indole-2-carboxylic acid derivative. The N-methyl compounds are made by reaction of the amides with $CH_3I$ and $K_2CO_3$ in DMF. The phenolic groups are sterically hindered and not readily alkylated. The acid used to prepare $R_5=$xiii has been synthesized by L. Grehn and U. Ragnarsson [J. Org. Chem., 46, 3492–3497 (1981)]. For $R_5=$xiv, the corresponding acids were prepared by T. T. Sakai, J. M. Rio, T. E. Booth and J. D. Glickson [J. Med. Chem., 24, 279–285 (1981)]. For $R_5=$xv, an excess of the appropriate commercially available ethylene glycol, polyethylene glycol, ethylene amine, or polyethylene amine is reacted with succinic anhydride or maleic anhydride to give the mono adduct carboxylic acids which can be used as the HCl or quaternary ammonium ($CH_3I$) salt when $X=N$. Dimers of 3 and ultimately of 6 can be formed where $R_5=$v, from commercially available dicarboxylic alkanes, or where $R_5=$xvi, preparing the requisite acids by reaction of the appropriate ethylene glycol or amine, or di, tri, or tetramer thereof, with excess succinic or maleic anhydride to afford the bis adduct dicarboxylic acid.

The acids used to prepare compounds where $R_5$ is xvii are known in the art or are obtained from the esters which are known in the art or can be prepared by generally known procedures. For example, the following acids and esters are known: 1H-benzimidazole-2-carboxylic acid [H. C. Ooi, H. Suschitzky, J. Chem. Soc. Perkin Trans. 1, 2871 (1982)]; 2-benzoxazolecarboxylic acid (H. Moeller, Justic Liebigs Ann. Chem., 749, 1 (1971)); 2-benzothiazolecarboxylic acid, ethyl ester (A. McKillop et al., Tetrahedron Letters 23, 3357 (1982)) and free acid (C. A. Reg. No. 3622-04-6); 2-benzofurancarboxylic acid (P. Bubin et al., Tetrahedron 37, 1131 (1981)); 5-amino-1H-indole-2-carboxylic acid, ethyl ester (C. A. Reg. No. 71086-99-2); 5-hydroxy-1H-indole-2-carboxylic acid (C. A. Reg. No. 21598-06-1); 5-hydroxybenzo[b]thiophene-2-carboxylic acid, methyl ester (C. A. Reg. No. 82788-15-6); 5-amino-benzo[b]thiophene-2-carboxylic acid (C. A. Reg. No. 20699-85-8). For xviii the acid 1H-indene-2-carboxylic acid is known in the art (J. Vebrel and R. Carrie, Bull. Soc. Chim. Fr. 116 (1982)) and corresponding substituted acids are obtained by procedures known in the art. When $R_5$ is xix the compounds are prepared using acids which are commercially available, e.g., 2-pyridinecarboxylic acid and piperazinecarboxylic acid or are otherwise known, e.g., 5-hydroxy-2-pyridinecarboxylic acid (C. A. Reg. No. 15069-92-8), 5-amino-2-pyridinecarboxylic acid (C. A. Reg. No. 24242-20-4) and 5-mercapto-2-pyridinecarboxylic acid (C. A. Reg. No. 24242-22-6). For $R_5=$xx, 2-naphthalenecarboxylic acid is commercially available, 6-hydroxy-2-naphthalenecarboxylic acid (C. A. Reg. No. 16712-64-4) and 6-amino-2-naphthalinecarboxylic acid, methyl ester (C. A. Reg. No. 5159-59-1) are known in the art and other suitable acids are prepared by general procedures known in the art. For $R_5=$xxi, quinaldic acid and 2-quinoxalinecarbonyl chloride are commercially available, 6-aminoquinaldic acid, methyl ester (C. A. Reg. No. 16606-1G-104) is known in the art and other suitably substituted acids are prepared by procedures generally known in the art. For $R_5=$xxii, the appropriate acids can be prepare as generally described by L. Grehn and U. Ragnarsson, J. Org. Chem. 46, 3492–3497 (1981).

Step 3:

The sulfonylation chemistry described herein is the case of $X=SO_2CH_3$. The mesylate (or, for example, tosylate) can be prepared under conditions known in the art employing pyridine (with or without a catalyst such as dimethylaminopyridine), or other acid acceptors such as trialkylamines (with solvent) and the corresponding sulfonyl chloride. The halogen analogs of 4 could be prepared under standard procedures known in the art such as $Ph_3P/CCl_4$, or $(CBr_4)$ or $CI_4$.

Step 4:

The O-deprotection step is described in detail for $R1=CH_2Ph$ in the following experiment. When $R_5=$acyl, however, it is usually more convenient to employ benzyl deprotection with in situ generated trimethylsilyl iodide in refluxing acetonitrile [G. A. Olah, S. C. Narang, B. G. B. Gupta and R. Malhotra, J. Org. Chem., 44, 1247 (1979)] than the conventional hydrogenation over palladium procedure known in the art. Analogs insoluble in acetonitrile may be reacted in mixed acetonitrile/benzonitrile at 60°–80° C.

O-Deprotection of other $R_1$ groups can be done by a number of procedures described in the art involving methyl ether cleavage, only alkyl mercaptide in hexamethylphosphorictriamide (HMPA) under an inert atmosphere (95°–110° C.) have been found to be effective [S. C. Welch and A. S. C. P. Rao, Tet. Letters, 505 (1977) and T. R. Kelly, H. M. Dali and W-G. Tsang, Tet. Letters, 3859 (1977), or $Me_2S.BBr_3$ in dichloroethane (P. G. Willard and C. B. Fryhle, Tet. Letters, 3731 (1980)].

Step 5:

For $R_5=$acyl this cyclization step is readily reversed during standard workup or chromatography on silica gel. Consequently the intermediate 5, when $R_5=$acyl, are readily isolable under mildly acidic conditions. Isolation of the cyclopropa- products 6 is done in the presence of excess anhydrous bases, such as triethylamine. In contrast, the $R_5=$sulfonyl analogs 6 are relatively more stable to acidic conditions.

Step 6:

Treatment of the cyclopropa- product 6, when $R_5=$acyl, with dilute aqueous base (0.1N NaOH or $CH_3NH_2$) readily saponifies the imide linkage to give the N-deprotected vinylogous amide 7 (within Formula I) as its conjugate anion. The novelty of this particular step is that the cyclopropyl ring of 7 is relatively stable under these conditions, unlike that of spiro(2,5)octa-1,4-diene-3-one [R. Baird and S. Winstein, J. Amer. Chem. Soc., 85, 567 (1963)].

Step 7: (see Chart III)

The alcohol function of the starting material 1 can be condensed, under conditions standard in the art, with the optically active, amino-protected amino acid, N-t-butoxy-carbonyl-L-tryptophan (commercially available), using a condensing agent such as ethyldimethylaminopropyl carbodiimide or dicyclohexyl-carbodiimide, with a catalytic amount of 4-dimethylaminopyridine in methylene chloride or other appropriate solvent. This affords a mixture of the shown ester diastereomers (Chart III), from which one diastereomer can be crystallized and separated from the other diastereomer using common organic solvents such as tetrahydrofuran and hexane.

Step 8:

Hydrolysis of the purified separated diastereomer of the tryptophane ester to the optically active alcohol 1 is achieved by conditions standard in the art (aqueous sodium hydroxide, methanol and tetrahydrofuran, ambient temperature, one hour). The optically active alcohol 1 may then be carried through the above described steps 1-5 to afford optically active analogs in exactly the manner described above for the racemic compounds.

Structures for exemplary starting and end product compounds, illustrating the above Chart II and Chart II process steps as set forth for each of detailed examples which follow in Chart I.

EXAMPLE 1

Step 1—N-Deprotection

To 200 mg. (0.52 mmol) of the N-mesyl indolinoindole, i.e., 1,2,3,6-tetrahydro-8-(methyl)-3-(methylsulfonyl)-5-(phenylmethoxy)-[1,2-b: 4,3-b']dipyrrole-5-methanol, in 10 ml. of dry THF and 10 ml. of toluene under $N_2$ was added, dropwise, 1.0 ml. (3.4 mmol) of 3.4M sodium bismethoxyethoxyaluminum hydride in toluene. The clear, colorless solution was quickly heated, and the condenser was lifted under a flow of nitrogen to allow THF to escape. After the internal temperature of the solution reached 85° (15 min.) the condenser was replaced and heating was continued for 15 min. The yellow solution was cooled, quenched with 10 ml. of 15% $K_2CO_3$, and diluted with ether and water. The colorless ether phase was separated, dried ($Na_2SO_4$) and stripped to 150 mg. of a nearly white foam, about 85% pure, of 1,2,3,6-tetrahydro-8-(methyl)-5-(phenylmethoxy)[1,2-b: 4,3-b']dipyrrole-1-methanol by NMR. If $CH_2Cl_2$ is used in the workup, the yield is substantially lower and the product is less pure.

NMR (CDCl$_3$: 8.33 (brs, 1H), 7.4 (m, 5H); 6.8 (brs. 1H); 6.23 (s, 1H); 5.02 (s, 2H); 3.8–3.5 (m, 5H); 2.92 (brs. 2H, OH, NH); 2.32 (s, 3H).

EXAMPLE 2

Step 2—N-amidation

The reaction described in Step 1 was carried out on 100 mg. (0.25 mmol) of the N-mesyl indolinoindole, except that $CH_2Cl_2$ was used instead of ether in the workup. The organic phase from that reaction which contains indolinoindole, i.e., 1,2,3,6-tetrahydro-8-(methyl)-5-(phenylmethoxy)[1,2-b: 4,3-b']dipyrrole-1-methanol, was dried ($Na_2SO_4$) and treated with 120 μl (1.2 mmol) of acetic anhydride. After 15 minutes the solution was concentrated and chromatographed on silica gel, eluting with 60% acetone/cyclohexane, to afford 52 mg. (0.148 mmol, 57%) of a white powder.

NMR (acetone-d$_6$): 10.17 (brs, 1H); 8.12 (s, 1H; 7.7–7.3 (m, 5H); 7.12 (m, 1H); 5.2 (s, 2H); 4.4–3.2 (m, 5H); 2.9 (brs, 1H, OH); 2.4 (s, 3H); 2.18 (s, 3H).

EXAMPLE 3

Step 2—N-Amidation

To 100 mg. (0.32 mmol) of indolinoindole in 7 ml. of DMF under $N_2$ were added 55 mg. (0.34 mmol) of indole-2-carboxylic acid and 65 mg. (0.34 mmol) of ethyldimethylaminopropyl carbodiimde (EDC). The mixture was stirred at 25° C. for 22 hours. It was quenched with 1M KHSO$_4$ and extracted twice with ethyl acetate. The organic phase was washed with water and brine and dried ($Na_2SO_4$). It was concentrated to 150 mg. (quantitative crude yield) of a yellow solid. A small amount precipitated from methylene chloride as a white solid on standing in the cold.

NMR (CDCl$_3$): 10.25 (brs, 1H); 8.5 (brs, 1H); (s, 1H); 7.73–6.95 (m, 11H); 5.16 (s, 2H); 4.86–4.35 (m, 2H); 3.95–3.55 (m, 3H); 2.38 (s, 3H).

M.S. (E.I.): m/e 451 (M+), 420, 360, 308, 277 (base peak), 144.

EXAMPLE 4

Step 2—N-Amidation

The reaction described in Step 1 was carried out on 127 mg. (0.33 mmol) of the N-mesyl indolinoindole, except that $CH_2Cl_2$ was used instead of ether in the workup. The organic phase from that reaction was dried ($Na_2SO_4$) and reacted with 38 μl (0.33 mmol) of benzoyl chloride and 46 μl (0.33 mmol) of triethylamine. After stirring for 30 minutes the reaction mixture was concentrated and chromatographed on silica gel, eluting with 40% acetone in cyclohexane. This afforded 61 mg. (0.15 mmol, 45% for two steps) of a nearly white powder.

NMR (CDCl$_3$): 8.5 (brs, 1H); 7.7–7.3 (m, 11H); 6.95 (brs, 1H); 5.17 [vbr (paramagnetic impurity), 2H]; 4.2–3.6 (brm, 5H); 2.38 (s, 3H).

EXAMPLE 5

Step 2—N-Amidation

To 70 mg. (0.23 mmol) of the indolinoindole in 5 ml. of DMF under $N_2$ were added 64 mg. (0.22 mmol) of 6-benzyloxy-7-methoxy indole-2-carboxylic acid and 45 mg. (0.24 mmol) of EDC. The mixture was stirred at 25° C. for three days. It was quenched with 1M KHSO$_4$ and extracted twice with ethyl acetate. The organic phase was washed with water and brine, dried (NaSO$_4$), and concentrated to 105 mg, of greenish oil. The NMR showed the desired product along with ~10% by weight of DMF, for a yield of ~70%.

NMR (acetone-d$_6$): 10.65 (brs, 1H); 10.2 (brs, 1H); 8.13 (s, 1H); 7.65–7.3 (m, 11HO; 7.1–6.95 (m, 3H); 5.2 (brs, 4H); 4.9–3.4 (m, ~5H); 2.4 (s, 3H).

M.S. (E.I.): m/e 587 (M+), 556, 496, 308, 280, 277 (base peak).

EXAMPLE 6

Step 2—N-Amidation

To 90 mg (0.29 mmol) of the indolinoindole in 6 ml of DMF under $N_2$ were added 60 mg (0.31 mmol) of 5-methoxyindole-2-carboxylic acid and 60 mg (0.31 mmol) of EDC. The reaction was stirred at 25° C. for 16 hrs. It was quenched with 1M KHSO$_4$ and extracted twice with ethyl acetate. The organic phase was washed with water and brine and dried (Na$_2$SO$_4$). It was concentrated in vacuo and chromatographed on silica gel, eluting with 10% acetone in methylene chloride. The product-containing fractions also contained DMF, and were diluted with methylene chloride, washed with water, dried (Na$_2$SO$_4$) and concentrated to 93 mg (0.19 mmol, 66%) of yellow solid.

NMR (CDCl$_3$): 10.2 (brs, 1H); 8.5 (brs, 1H); 8.05 (s, 1H); 7.3 (brs, 5H); 7.2–6.8 (m, 5H); 5.02 (s, 2H); 4.8–3.3 (m, 5H); 3.75 (s, 3H); 2.6 (brs, 1H, OH); 2.28 (brs, 3H).

M.S. (E.I.): m/e 481 (M+), 450, 390, 308, 277 (base peak), 174, 146.

EXAMPLE 7

Step 2—N-Amidation

To 90 mg (0.29 mmol) of the indolinoindole in 7 ml of DMF under N$_2$ were added 95 mg (0.30 mmol) of 5-(indol-2-ylcarbonylamino)-indole-2-carboxylic acid and 68 mg (0.34 mmol) of EDC. The reaction was stirred at 25° for 3 days. It was quenched with 1M KHSO$_4$ and extracted twice with ethyl acetate. The organic phase was washed with water and brine, dried (Na$_2$SO$_4$), and stripped to 186 mg of a dark, granular solid. This was dissolved in a small amount of pyridine. Dilution with methylene chloride precipitated a light yellow, flocculent solid (130 mg, 0.21 mmol, 72%).

NMR (DMSO-d$_6$) (broadened spectrum): 11.8 (brs, 2H); 10.95 (brs, 1H); 10.3 (brs, 1H); 8.3 (brs, 1H); 8.0–7.1 (m, ~15H); 5.3 (brs, 2H); 5.1 (vbr, ~1H); 4.7 (vbr, ~2H); 3.7 (vbr, ~2H); 2.4 (brs, ~3H).

M.S. (E.I.): 609 (M+), 593, 577, 465, 444, 319, 290, 276, 275, 176, 158, 144, 132 (base peak).

(FAB, glycerol): 610 (M+H+), 302, 287, 186, 144.

EXAMPLE 8

Step 2—N-Amidation

To 100 mg (0.32 mmol) of the indolinoindole in 7 ml of DMF under N$_2$ were added 90 mg (0.32 mmol) of 5-benzoylamino-indole-2-carboxylic acid and 65 mg (0.34 mmol) of EDC. The reaction was stirred at 25° for 3 days. It was quenched with 1M KHSO$_4$ and extracted twice with ethyl acetate. The opaque organic phase was washed with water and brine, dried (Na$_2$SO$_4$), and concentrated.

NMR (pyridine-d$_6$): 12.0 (brs, 1H); 10.9 (brs, 1H); 8.83 (s, 1H); 8.62 (s, 1H); 8.45–8.32 (d of d, 2H); 8–7.75 (m, 2H); 7.53–7.3 (m, ~11H); 5.3 (brs, 3H); 4.85 (vbr, ~1H); 4.4–3.9 (m, ~3H); 2.54 (s, ~3H).

EXAMPLE 9

Step 2—N-Amidation

To 48 mg (0.155 mmol) of the indolinoindole in 6 ml of DMF under N$_2$ were added 68 mg (0.155 mmol) of the 5-amido substituted indole-2-carboxylic acid and 31 mg (0.155 mmol) of EDC. The reaction was stirred at 25° for 2 days. It was quenched with 1M KHSO$_4$ and extracted twice with ethyl acetate. The opaque organic phase was washed with water and brine, dried (Na$_2$SO$_4$), and concentrated to 105 mg (0.144 mmol, 93%) of a light brown solid.

NMR (pyridine-d$_6$): 13.3 (vbr, ~1H); 12.8 (brs, 1H); 12.05 (brs, 1H); 10.97 (s, 1H); 10.88 (s, 1H); 8.9 (s, 1H); 8.64 (s, 1H); 8.45–8.33 (d of d, 2H); 8–7.75 (m, ~5H); 7.55–7.3 (m, ~11H); 5.28 (brs, ~3H); 4.75–3.8 (vbr, ~4H); 2.5 (s, ~3H).

EXAMPLE 10

Step 2—N-Amidation

To 100 mg (0.32 mmol) of the indolinoindole in 7 ml of DMF under N$_2$ were added 70 mg (0.22 mmol) os 5-ureido-indole-2-carboxylic acid and 65 mg (0.34 mmol) of EDC. The reaction was stirred at 25° for 4 days. It was quenched with 1M KHSO$_4$ and extracted twice with ethyl acetate. The organic phase was washed with water and brine, dried (Na$_2$SO$_4$) and concentrated to 140 mg (0.27 mmol, 86%) of a green-tainted white solid.

NMR (pyridine-d$_5$): 12.75 (brs, 1H); 12.1 (brs, 1H); 9.65 (s, 1H); 8.65 (s, 1H); 8.53 (s, 1H); 7.75–7.2 (m, 9H); 6.65 (brs, 2H); 5.28 (s, 2H); 4.85–3.85 (brm, ~5H); 2.55 (s, 3H).

EXAMPLE 11

Step 2—N-Amidation

To 71 mg (0.23 mmol) of the indolinoindole in 5 ml of DMF under N$_2$ were added 88 mg (0.23 mmol) of the ureido-bis indolic acid and 45 mg (0.23 mmol) of EDC. The reaction was stirred at 25° for 2 days. It was quenched with 1M KHSO$_4$ and extracted twice with ethyl acetate. The organic phase was washed with brine. A brown emulsive layer was diluted with acetone, filtered, and the filtrate combined with the organic phase and dried (Na$_2$SO$_4$). It was concentrated in vacuo to 135 mg (0.20 mmol, 88% crude yield) of a greenish-grey solid.

NMR (pyridine-d$_5$): 13.25 (brs, 1H); 13.0 (brs, 1H); 12.2 (brs, 1H); 11.16 (brs, 1H); 9.8 (brs, 1H); 8.9 (s, 1H); 8.62 (s, 1H); 8.5 (s, 1H); 8.2–7.35 (m, 12H); 5.28 (brs, ~3H); 4.8–3.8 (brm, ~4H); 2.55 (s, ~3H).

EXAMPLE 12

Step 2—N-Amidation

A 60 mg (0.19 mmol) quantity indolinoindole was dissolved with stirring under N$_2$ at RT in 4 ml DMF. Added 38 mg (0.22 mmol) quinaldic acid and 40 mg (0.20 mmol) EDC. Left to react for 22 hrs, when the reaction mixture was diluted with CH$_2$Cl$_2$. The solution was washed with 5% NaHSO$_4$, 5% NaHCO$_3$ and brine, backextracting with CH$_2$Cl$_2$. The organic phases were dried over Na$_2$SO$_4$ and evaporated, leaving a brown oil.

The crude product was chromatographed over 100 g silica gel, eluting with a gradient of 50% EtOAc–50% hexane to 80% EtOAc–20% hexane. Fractions of 20 ml were collected, analyzing them by TLC. Fractions 32–42 contained the major product and were combined and evaporated, leaving 80 mg (91% yield) yellow solid.

TLC: Silica gel; UV visualization.

| 50% acetone–50% CH$_2$Cl$_2$ | 50% EtOAc–50% hexane |
|---|---|
| R$_f$ = 0.92 | R$_f$ = 0.39 |

NMR: (CDCl$_3$, TMS, δ); 2.2 (s, 3H); 2.1–2.5 (broad, 1H); 3.4–3.8 (m, 3H); 4.2–4.7 (m, 2H); 5.1 (s, 2H); 6.8 (broad, 1H); 7.2–8.2 (m, 12H); 8.4 (broad, 1H).

EXAMPLE 13

Step 2—N-Amidation

A 0.26 mmol quantity indolinoindole was stirred at RT under N$_2$ in 5 ml dry DMF. Added 32 mg (0.29 mmol) pyrrole-2-carboxylic acid and 52 mg (0.26 mmol) EDC. Left to react for 23 hrs, when the reaction mixture was diluted with $CH_2Cl_2$ and washed with 5% $NaHSO_4$, 5% $NaHCO_3$ and brine, backextracting with $CH_2Cl_2$. The organic phases were dried over $Na_2SO_4$ and evaporated under vacuum.

The crude product was chromatographed over 15 g silica gel, eluting with 250 ml 50% EtOAc-50% hexane, followed by 100 ml 60% EtOAc-40% hexane. Fractions of 5 ml were collected, analyzing them by TLC. Fractions 14–40 contained the product spot and were combined and evaporated, leaving 76 mg (73% yield) solid.

TLC: Silica gel; UV visualization; 50% EtOAc-50% hexane; $R_f$ 0.31.

NMR: ($CDCl_3$, $d_4$-MeOH; TMS, $\delta$); 2.4 (s, 3H); 2.7–3.0 (m, 2H); 3.4–4.8 (m, 5H); 5.2 (s, 2H); 6.3 (broad, 1H); 6.8 (broad, 1H); 6.95 (broad, 1H); 7.3–7.6 (m, 5H); 8.0 (s, 1H); 8.85 (broad, 1H); 10.2 (broad, 1H).

EXAMPLE 14

Step 3—O-Sulfonylation

The crude product from the reaction of 1 mmol of the indolinoindole with acetic anhydride (Step 2) was dissolved in 4 ml of distilled (NaOH) pyridine and ~10 mg of recrystallized dimethylaminopyridine (DMAP) was added. The solution was purged with $N_2$, and 250 $\mu$l (3.2 mmol) of methanesulfonyl chloride (MsCl) was added. After 20 min of stirring at 25°, the reaction was quenched with 10% HCl and extracted with ethyl acetate. The organic phase was dried ($Na_2SO_4$) and treated with decolorizing charcoal for 2 hr. Filtration afforded a yellow solution containing two components. The main component was the desired mesylate. The minor product was the acetate ester. This was saponified (NaOH, $EtOH/H_2O$, 10 min) and mesylated as above. The total yield of product was 242 mg (57%).

NMR (DMSO-$d_6$): 11.0 (brs, 1H); 7.97 (s, 1H); 7.6–7.4 (m, 5H); 7.18 (s, 1H); 5.27 (s, 2H); 4.5–4.0 (m, 5H); 3.16 (s, 3H); 2.38 (s, 3H); 2.2 (s, 3H).

EXAMPLE 15

Step 3—O-Sulfonylation

To 150 mg (0.32 mmol) of the alcohol substrate in 3 ml of methylene chloride and 3 ml of dry pyridine under $N_2$ were added ~5 mg of DMAP and 100 $\mu$l (1.3 mmol) of MsCl. After 10–15 min of stirring at 25°, the reaction was quenched with 10% HCl and extracted with ethyl acetate. The organic phase was washed with more 10% HCl, then brine, and dried ($Na_2SO_4$). It was concentrated to 158 mg (0.3 mmol, 93%) of grey-blue solid.

NMR (acetone-$d_6$): 10.9 (brs, 1H); 10.4 (brs, 1H); 8.1 (s, 1H); 7.8–7.1 (m, 11H); 5.25 (s, 2H); 4.8–4.13 (m, 5H); 2.97 (s, 3H); 2.47 (s, 3H).

EXAMPLE 16

Step 3—O-Sulfonylation

To 61 mg (0.15 mmol) of the alcohol substrate in 1 ml of dry pyridine under $N_2$ was added 25 $\mu$l (0.32 mmol) of MsCl. After stirring for 2 hr at 25°, the reaction was quenched with 10% HCl and extracted with $CH_2Cl_2$. The organic phase was dried ($Na_2SO_4$) and concentrated to 77 mg (quantitative crude yield) of an impure, foamy solid.

NMR (acetone-$d_6$): 10.3 (brs, 1H); 7.7–7.3 (m, 11H); 7.14 (brs, 1H); 5.1 [brs (paramagnetic impurity), 2H]; 4.55–4.0 (m, 5H); 2.92 (s, 3H); 2.4 (s, 3H).

EXAMPLE 17

Step 3—O-Sulfonylation

To 58 mg (0.1 mmol) of the alcohol substrate in 1 ml of methylene chloride and 1 ml of dry pyridine under $N_2$ were added ~5 mg of DMAP and 50 $\mu$l (0.65 mmol) of MsCl. After 25 min of stirring at 25°, the reaction was quenched with 10% HCl and extracted with ethyl acetate. The organic phase was washed with more 10% HCl, then brine, dried ($Na_2SO_4$), and stripped to 73 mg (quantitative crude yield) of a semicrystalline film.

NMR (acetone-$d_6$+MeOH-$d_4$): 7.87 (brs, 1H); 7.55–7.3 (m, 11H); 7.1–6.93 (m, 3H); 5.19 (s, 2H); 5.15 (s, 2H); 4.7–4 (m, 5H); 3.98 (s, 3H); 2.87 (s, 3H); 2.4 (s, 3H). (Not examined beyond $\delta$ 10.5).

EXAMPLE 18

Step 3—O-Sulfonylation

To 88 mg (0.18 mmol) of the alcohol substrate in 2 ml of methylene chloride and 2 ml of dry pyridine under $N_2$ were added ~4 mg of DMAP and 55 $\mu$l (0.71 mmol) of MsCl. After 15 min of stirring at 25°, the reaction was quenched with 10% HCl and extracted with ethyl acetate. The organic phase was washed with 10% HCl and brine and dried ($Na_2SO_4$). The initially almost colorless solution became a dark blue-grey upon concentration in vacuo, affording 112 mg (quantitative crude yield) of blue-grey solid.

NMR (acetone-$d_6$): 10.3 (brs, 1H); 8.1 (s, 1H); 7.56–7.1 (m, 9H); 7.02–6.88 (d of d, 1H); 5.17 (s, 2H); 4.8–4 (m, ~5H); 3.97 (s, ~3H); 2.95 (s, 3H); 2.45 (s, 3H). (Not examined beyond $\delta$ 10.5).

EXAMPLE 19

Step 3—O-Sulfonylation

To 120 mg (0.2 mmol) of the alcohol substrate in 5 ml of dry pyridine under $N_2$ were added ~5 mg of DMAP and 75 $\mu$l (1 mmol) of MsCl. After 10 min of stirring at 25°, the mixture was concentrated in vacuo, quenched with 10% HCl, and extracted twice with ethyl acetate. The organic phase was washed with brine, dried ($Na_2SO_4$) and stripped to 123 mg (0.18 mmol, 90% crude yield).

NMR (acetone $d_6$): 11.1 (vbr, ~1H); 10.3 (brs, ~1H); 9.8 (s, 1H); 8.43 (s, 1H); 8.1 (s, 1H); 7.76–7.14 (m, ~15H); 5.21 (s, 2H); 4.8–4.1 (brm, ~5H); 2.94 (s, 3H); 2.41 (s, 3H).

EXAMPLE 20

Step 3—O-Sulfonylation

The crude product obtained from the EDC coupling (Step 2) of 0.32 mmol of the indolinoindole and an equivalent of 5-benzoylamino-indole-2-carboxylic acid was dissolved in 5 ml of dry pyridine under $N_2$. To this were added ~5 mg of DMAP and 150 $\mu$l (2 mmol) of MsCl. After 50 min of stirring at 25°, the reaction was quenched with 10% HCl and extracted twice with ethyl acetate. The organic phase was washed with water and brine, dried ($Na_2SO_4$), and concentrated to 160 mg (0.25 mmol, 77% crude yield for two steps) of green-tainted solid.

NMR (acetone-$d_6$): 11.0 (brs, 1H); 10.3 (brs, 1H); 9.6 (s, 1H); 8.4 (s, 1H); 8.1 (m, 3H); 7.65–7.3 (m, 10H); 7.15 (brs, 2H); 5.16 (s, 2H); 4.8–4.0 (m, ~5H); 2.92 (s, 3H); 2.4 (brs, 3H).

EXAMPLE 21

Step 3—O-Sulfonylation

To 105 mg (0.14 mmol) of the alcoholic substrate in 5 ml of dry pyridine under $N_2$ were added ~5 mg of DMAP and 100 μl (1.3 mmol) of MsCl. After 3 hr of stirring at 25°, the reaction was quenched with 10% HCl and extracted twice with ethyl acetate. The organic phase was washed with water and brine, dried ($Na_2SO_4$) and concentrated to 102 mg (0.13 mmol, 88% crude yield) of a dark solid.

NMR (acetone-$d_6$): 11.3 (brs, 1H); 11.15 (brs, 1H); 10.3 (brs, 1H); 9.73 (s, 1H); 9.55 (s, 1H); 8.43 (s, 1H); 8.31 (s, 1H); 8.1 (m, 3H); 7.65–7.3 (m, 13H); 7.1 (brs, 2H); 5.12 (s, 2H); 4.8–4 (m, ~5H); 2.9 (s, 3H); 2.35 (brs, 3H).

EXAMPLE 22

Step 3—O-Sulfonylation

To 140 mg (0.27 mmol) of the alcohol substrate in 5 ml of dry pyridine under $N_2$ were added ~5 mg of DMAP and 150 μl (2 mmol) of MsCl. After 3 hr of stirring at 25°, the reaction was quenched with 10% HCl and extracted twice with ethyl acetate. The organic phase was washed with water and brine and dried ($Na_2SO_4$). The product was concentrated and chromatographed on silica gel, eluting with 50% acetone in cyclohexane. The first eluted product ($R_f$=0.35 in 50% acetone/cyclohexane) was the cynamide (63 mg, 0.11 mmol, 41%).

NMR (acetone-$d_6$): 11.0 (brs, 1H); 10.3 (brs, 1H); 8.64 (s, 1H); 8.1 (s, 1H); 7.68–7.3 (m, 7H); 7.2–7.03 (m, 3H); 5.22 (s, 2H); 4.85–3.9 (m, ~5H); 2.95 (s, 3H); 2.45 (s, 3H).

M.S. (F.A.B., glycerol+thioglycerol): 588 ($M+H_2O+H^+$); 570 ($M+H^+$), 510, 492, 474, 199, 187, 102, 91.

The second eluted product was the ureido compound (34 mg, 0.058 mmol, 21%).

NMR (pyridine-$d_5$): 12.8 (brs, 1H); 12.25 (brs, 1H); 9.55 (s, 1H); 8.52 (s, 2H); 7.8–7.2 (m, 9H); 6.57 (brs, 2H); 5.26 (s, 2H); 4.95–4.3 (m, 5H); 3.08 (s, 3H); 2.55 (s, 3H).

M.S. (F.A.B., glycerol+thioglycerol): 588 ($M+H^+$); 510, 492, 126, 91.

EXAMPLE 23

Step 3—O-Sulfonylation

To 135 mg (0.20 mmol) of the alcohol substrate in 4 ml of dry pyridine under $N_2$ were added ~5 mg of DMAP and 150 μl (2 mmol) of MsCl. After stirring for 1 hr at 25°, the reaction was quenched with 10% HCl and extracted twice with ethyl acetate. The organic phase was washed with more 10% HCl and with brine and dried ($Na_2SO_4$). The organic phase was concentrated to ~15 ml, and ~0.3 ml of concentrated sulfuric acid was added with stirring (to hydrolyze the cyanamide to the urea). After ~1 min the yellow-brown solution was diluted with ethyl acetate and washed with water. The aqueous phase was re-extracted with ethyl acetate, and the combined organic phases were washed with brine and dried ($Na_2SO_4$). Concentration and chromatography on silica gel with 50% acetone in methylene chloride afforded 39 mg (0.052 mmol, 26% of a faintly yellow crystalline solid).

NMR (pyridine-$d_5$): 13.1 (brs, ~1H); 12.98 (brs, ~1H); 12.28 (brs, 1H); 10.9 (s, 1H); 9.5 (s, 1H); 8.82 (1H, shoulder on pyridine signal); 8.53 (s, 1H); 8.47 (s, 1H); 8.0 (m, 1H); 7.77–7.3 (m, 11H); 6.55 (brs, 2H); 5.27 (s, 2H); 5–4.3 (m, ~5H); 3.13 (s, 3H); 2.55 (s, 3H).

EXAMPLE 24

Step 3—O-Sulfonylation

A 241 mg quantity (0.52 mmol) alcohol was dissolved with stirring at RT under $N_2$ in 5 ml dry pyridine. Syringed in 210 ml (excess) mesyl chloride and left to react for 6 hours. Added a few drops of 5% $NaHSO_4$ and then partitioned between $CH_2Cl_2$-5% $NaHSO_4$. The layers were separated and the organic phase dried over $Na_2SO_4$ and evaporated, leaving 286 mg brown solid (100% yield).

TLC: Silica gel; UV visualization; 50% EtOAc-50% hexane; $R_f$: 0.65.

NMR: ($CDCl_3$, TMS, δ): 2.4 (s, 3H); 2.8 (s, 3H); 3.8–4.8 (m, 5H); 5.3 (s, 2H); 7.0 (broad, 1H); 7.2–8.6 (m, 13H).

EXAMPLE 25

Step 3—O-Sulfonylation

A 76 mg quantity (0.19 mmol) alcohol and 2 ml dry pyridine were stirred at RT under $N_2$. Syringed in 70 μl (excess) mesyl chloride and left to react for 4 hours. Added a few drops of 5% $NaHSO_4$ and then partitioned the reaction mixture between $CH_2Cl_2$-5% $NaHSO_4$. Separated the layers and dried the organic phase over $Na_2SO_4$, evaporating it under vacuum. This left 97 mg brown solid (100% crude yield).

TLC: Silica gel; UV visualization; 50% EtOAc-50% hexane; $R_f$: 0.69.

NMR: ($CDCl_3$, TMS, δ): 2.4 (s, 3H); 2.8 (s, 3H); 3.5–4.8 (m, 5H); 5.2 (s, 2H); 6.3 (broad, 1H); 6.75 (broad, 1H); 6.9 (broad, 2H); 7.2–7.9 (m, 4H); 8.0 (broad, 1H); 8.6 (broad, 1H); 10.2 (broad, 1H).

EXAMPLE 26

Step 4—O-Deprotection

The reaction described in Step 3 was carried out on 52 mg (0.148 mmol) of the N-acetyl indolinoindole to afford 63 mg of crude mesylate as a purple-tinted white solid. This was dissolved in 10 ml of DMF and slurried with 0.5 teaspoonful of activated Raney nickel in ethanol for 20 min. To the filtered solution was added 36 mg of Pd/C, and the mixture was shaken under $H_2$ for 50 min. The mixture was filtered through Celite, washing with DMF, and concentrated in vacuo. The crude product in DMF was treated with 70 μl of ethyldiisopropylamine for about 10 min (Step 5, in the expectation of forming the cyclopropylspirodienone) and rapidly chromatographed (50% acetone/cyclohexane eluant). Upon standing at 4° overnight, the product-containing fractions deposited white granular crystals (10 mg, 0.03 mmol, 20%) identified as the uncyclized phenol mesylate.

NMR (DMSO-$d_6$): 7.6 (s, 1H); 7.0 (s, 1H); 4.4–3.8 (m, 5H); 3.12 (s, 3H); 2.32 (s, 3H); 2.15 (s, 3H).

MS: (E.I.): m/e [338 ($M^+$), not found]; 242 (M-$HSO_3Me$), 228, 213, 200, 186, 96, 79.

EXAMPLE 27

Step 5—Cyclization-Cyclopropa[c]pyrrolo[3,2-e]indol-4(5H)-one, 2-acetyl-1,2,8,8a-tetrahydro-7-methyl- The mother liquors from the fractions which had yielded the phenolic mesylate described in Step 4 (that reaction product had been briefly reacted with ethyldiisopropyl amine, vide infra) were recrhomatographed on silica gel, eluting with 50% acteone/cyclohexane, to afford 10 mg. of a powdery white solid identified as the cyclopropyl spirodienone (0.04 mmol, 30% from the N-acetyl alcohol).

NMR (DMSO-$d_6$, 200 MHz, 70° C.): 6.8 (s, 1H); 6.67 (s, 1H); 4.08 (dd, 1H, $J_{c,d}$~10 Hz); 4.02 (dd, 1H, $J_{cd}$~10 Hz, $J_{d,e}$~fHz); 3.03 (m, 1H); 2.17 (s, 3H); 1.96 (s, 3H); 1.89 (dd, 1H, $J_{e,f}$~8 Hz, $J_{f,g}$~4 Hz); 1.23 (dd, 1H, $J_{e,g}$~4 Hz, $J_{f,g}$~4Hz).

MS: (E.I.): m/e 242 (M+); 200, 199, 185, 171, 156.

UV: (MeOH) $\lambda_{max}$, 348 nm (E=14,000), 284 nm (E=18,100).

Following procedures described hereinabove, using stoichiometric equivalent amounts of the N-decanoylindolinoindole, N-hexadecanoylindolinoindole, and N-licosanoylindolinoindole, in place of the N-acetylindolinoindole in Example 26, and then cyclizing the product thereof as in Example 27 there can be formed the following analogous compounds, respectively:

1,2,8,8a-tetrahydro-7-methyl-2-decanoyl-cyclopropa[c]pyrrolo[3,2-e]endol-4(5H)-one, 1,2,8,8a-tetrahydro-7-methyl-2-hexadecanoylcyclopropa[c]pyrrolo[3,2,e]indol-one, and 1,2,8,8a-tetrahydro-7-methyl-2-eicosanoylcyclopropa[c]pyrrolo[3,2-e]indol-4(5H)-one.

EXAMPLE 28

Step 4—O-Deprotection; Step 5—Cyclization-Cyclopropa[c]pyrrolo[3,2-e]indol-4(5H)-one, 1,2,8,8a-tetrahydro-2-[(1H)-indol-2-ylcarbonyl)]-7-methyl- To 162 mg (0.30 mmol) of the protected mesylate and 150 mg (1 mmol) of dry NaI in 6 ml of distilled ($CaH_2$) acetonitrile under $N_2$ was added 130 µl (1 mmol) of distilled trimethylsilyl chloride (TMS-Cl). The mixture was heated to reflux and stirred for 10 min. The reaction was cooled, diluted with ethyl acetate, and washed with 0.1M sodium thiosulfate. The organic phase was washed with water and brine and dried ($Na_2SO_4$). Distilled triethylamine (200 µl) was added and the solution, after 15 min, was concentrated. DMF (100 µl) was added to dissolve the brown precipitate which formed, and another 100 µl of triethylamine was added. The mixture was chromatographed on silica gel, eluting with 50% acetone in cyclohexane containing 100 µl of triethylamine for every 100 ml of eluant. The product-containing fractions were concentrated to 49 mg of a light tan solid. This was dissolved in acetone and chilled. Two crops of cream colored precipitate were obtained, together weighing 17.2 mg (0.05 mmol, 17%). Rechromatography of the mother liquor gave 12 mg of impure product.

NMR (DMSO-$d_6$): 11.82 (brs, 1H); 11.55 (brs, 1H); 7.8–7.15 (m, 5H); 6.95 (m, 1H); 6.72 (s, 1H); 4.45 (m, 2H); 3.2 (m, 1H); 2.0 (brs, 4H); 1.38 (t, 1H, J~4 Hz).

M.S. (E.I.): 343 (M+), 326, 200, 199, 144.

UV: (1% DMF in MeOH) $\lambda_{max}$362 nm ($\epsilon$=22,000), 310 nm ($\epsilon$=22,000).

EXAMPLE 29

Step 4—O-Deprotection

To 77 mg (0.15 mmol) of the crude mesylate from Step 3 was added 5 ml of a slurry of activated Raney nickel in DMF. After 40 min the mixture was filtered, washing the catalyst with DMF. To this solution (~35 ml) was added 53 mg of 10% Pd/C and the mixture was hydrogenated (14 psi) on a Parr apparatus for 3 hr. The mixture was then filtered, washing the catalyst with DMF, and the DMF was removed in vacuo. To the residue was added 10 ml of $CH_2Cl_2$. A dark solid precipitated. The mixture was treated with ethyl diisopropylamine (75 µl, 0.43 mmol) overnight at 4°; it remained largely heterogeneous however. It was chromatographed on silica gel, eluting with 30% acetone in cyclohexane, to afford 14 mg (0.035 mmol, 23%) of a white granular solid.

NMR (DMSO-$d_6$): 9.73 (s, 1H): 7.45 (m, 6H); 7.05 (s, 1H); 4.43–3.67 (m, 5H); 3.03 (s, 3H); 2.3 (s, 3H).

EXAMPLE 30

Step 5—Cyclization-Cyclopropa[c]pyrrolo[3,2-e]indol-4(5H)-one, 2-benzoyl-1,2,8,8a-tetrahydro-7-methyl- To 13 mg (0.033 mmol) of the phenolic mesylate in 0.4 ml of DMSO-$d_6$ and ~5 ml of $CH_2Cl_2$ was added 50 µl (0.28 mmol) of ethyldiisopropylamine. After 30 min, the reaction was diluted with $CH_2Cl_2$, washed with water, and dried ($Na_2SO_4$) and concentrated. The residue was stripped in vacuo from 50% acetone in cyclohexane to afford 7 mg of a white solid.

NMR (DMF-$d_7$): 7.6 (m, 5H); 6.98 (m, 1H); 5.85 (s, 1H); 4.3–3.8 (m, 2H); 3.05 (m, 1H); 2.03 (s, 3H); 2.0 (m, 1H); 1.6 (t, 1H, J=4 Hz).

UV: (MeOH) $\lambda_{max}$352 nm (E=14,600), 288 nm (E=14,900).

EXAMPLE 31

Step 4—O-Deprotection

To 66 mg (0.1 mmol) of the protected mesylate was added activated Raney nickel in 30 ml of DMF and 5 ml of ethanol. After 40 min, the mixture was filtered, washing the catalyst with DMF. The resulting yellow solution was hydrogenated on a Parr apparatus (19 psi) with 140 mg of Pd/C for 4 hr. The mixture was filtered and the solution concentrated to ~3 ml. It was diluted with $CH_2Cl_2$, washed with water, dried ($Na_2SO_4$), concentrated, and chromatographed, to afford 10 mg (26%) of a nearly white solid.

NMR (acetone-$d_6$): 10.3 (vbr, ~1H); 10.0 (vbr, <1H); 9.85 (vbr, <1H); 7.88 (s, 1H); 7.4–6.8 (m, 4H); 4.73–4.1 (m, 5H); 3.97 (s, 3H); 3.0 (s, ~3H); 2.45 (s, 3H).

EXAMPLE 32

Step 5—Cyclization-Cyclopropa[c]pyrrolo[3,2-e]indol-4(5H)-one, 1,2,8,8a-tetrahydro-2-[(6-hydroxy-7-methoxy-1H-indol-2-yl)carbonyl]-

To 10 mg (0.026 mmol) of the uncyclized mesylate in ~0.4 ml of DMSO-$d_6$ and 2 ml of $CH_2Cl_2$ was added 60 µl of ethyldiisopropylamine. The reaction was concentrated in vacuo (to remove excess amine), diluted with $CH_2Cl_2$, and washed with water. The organic phase was dried ($Na_2SO_4$) and concentrated, and the residue dissolved in ~0.4 ml of acetone-$d_6$ for NMR analysis, which showed product as well as ammonium salt present. The product crystallized in the NMR tube, affording ~5 mg of pure product.

NMR (DMSO-$d_6$): 11.5 (brs, 1H); 11.3 (brs, 1H); 9.2 (s, 1H); 7.28 (d, 1H, J~9 Hz); 7.11 (s, 1H); 6.94 (s, 1H); 6.79 (d, 1H, J~9 Hz); 6.51 (s, 1H); 4.38 (m, 2H); 3.75 (s, ~3H); 3.15 (m, 1H); 2.02 (s, 3H); 1.96 (m, 1H); 1.42 (m, 1H).

M.S. (E.I.): m/e 389 (M+), 372, 281, 207, 201, 190, 147, 134.

F.A.B., glycerol: 392 (M+ +H+H$_2$), 203, 202, 201, 190, 187.

UV: (0.5% DMF in MeOH) $\lambda_{max}$371 nm ($\epsilon$=23,000), 322 nm ($\epsilon$=15,000), 293 nm ($\epsilon$=13,000).

EXAMPLE 33

Step 4—O-Deprotection; Step 5—Cyclization-Cyclopropa[c]pyrrolo[3,2-e]indol-4(5H)-one, 1,2,8,8a-tetrahydro-2-[(5-methoxy-1H-indol-2-yl)carbonyl]-

Steps 2 and 3 were carried out on 90 mg (0.29 mmol) of the indolinoindole without isolation of the intermediates. The protected mesylate, in 30 ml of ethyl acetate, was treated with ~10 cm$^3$ of activated Raney nickel in 100 ml of ethanol. After 30 min, the mixture was filtered and the filtrate was concentrated. The residue was diluted with ethyl acetate and washed with water, then brine, dried (Na$_2$SO$_4$) and concentrated to ~30 ml. To this was added 100 ml of ethanol and 140 mg of Pd/C and the mixture was hydrogenated on a Parr apparatus (17 psi) for 1 hr. No reaction occurred, so the suspension was again treated with Raney nickel, filtered, concentrated, dissolved in ethyl acetate, washed with water and brine, dried, concentrated, diluted with ethanol and hydrogenated for 45 min with 90 mg Pd/C. Reaction occurred. The mixture was filtered, concentrated, and dissolved in 2 ml of DMF. It was diluted with ~5 ml of ethyl acetate and 200 µl of ethyldiisopropylamine was added. After 75 min, the mixture was diluted with ethyl acetate, washed with dilute NH$_4$Cl and brine, dried (Na$_2$SO$_4$) and concentrated. Chromatography on silica gel, eluting with 50% acetone in cyclohexane, afforded 11.6 mg (0.03 mmol, 11% for Steps 2-5) of a light yellow solid.

NMR (DMSO-d$_6$): 11.7 (brs, 1H); 11.55 (brs, 1H); 7.45 (d, 1H, J=9 Hz); 7.2-6.9 (m, 4H); 6.7 (s, 1H); 4.44 (m, 2H); 3.78 (s, 3H); 3.12 (m, 1H); 2.00 (s, 3H); 1.96 (m, 1H); 1.36 (t, 1H).

M.S.: Calc. for C$_{22}$H$_{19}$N$_3$O$_3$: 373.1426; found: 373.1404.

UV (1% DMF in MeOH): $\lambda_{max}$363 nm ($\epsilon$=19,000), 311 nm ($\epsilon$=17,000).

EXAMPLE 34

Step 4—O-Deprotection; Step 5—Cyclization-1,2,8,8a-tetrahydro-7-methyl-2-[[5-[[[1H-indol-2-yl]carbonyl]amino]-1H-indol-2-yl]carbonyl]cyclopropa[c]pyrrolo[3,2-e]indol-4(5H)-one To 220 mg (0.32 mmol) of the protected mesylate and 190 mg (1.27 mmol) of dry sodium iodide under N$_2$ were added 6 ml of dry acetonitrile and 2 ml of dry benzonitrile. Trimethylsilylchloride (160 µl, 1.26 mmol) was then introduced and the mixture was heated to 65° for 45 min. Reaction was still incomplete, so 100 mg (0.67 mmol) of NaI and 80 µl (063 mmol) of TMS-Cl were added, and the mixture was heated to reflux for 15 min. The mixture was cooled, diluted with ethyl acetate, and washed with 0.1M sodium thiosulfate, then with brine, and dried (Na$_2$SO$_4$). The solution was concentrated to an oil (benzonitrile). Addition of 100 µl of dry triethylamine afforded a semi-solid, which was diluted with ethyl acetate and washed with water, dried (Na$_2$SO$_4$) and concentrated. A small amount of DMF was added to dissolve the resulting suspension, and the oil was chromatographed on silica gel, eluting with 50% acetone in cyclohexane and gradually increasing the acetone content of the eluant. The purest fractions were combined and stripped to ~50 mg of an off-white solid. This was dissolved in ~3 ml of acetone and 20 µl of triethylamine was added. A light yellow solid precipitated (23.5 mg) and was washed and collected. The mother liquor and less pure chromatography fractions were combined and again dissolved in a small volume of acetone and 20 µl of triethylamine. A second crop of product precipitated and was washed and collected (24 mg; total yield 47.5 mg, 0.095 mmol, 30%). Both crops had the same extinction coefficients on UV analysis.

NMR (DMSO-d$_6$): 11.9 (brs, 1H); 11.8 (brs, 1H); 10.33 (s, 1H); 8.3 (s, 1H); 7.8-6.97 (m, 10H); 6.78 (s, 1H); 4.5 (m, 2H); 3.14 (m, 1H); 2.03 (s, 3H); 1.96 (m, 1H); 1.42 (m, 1H).

M.S. (F.A.B., glycerol): 504 (M+H+H$_2$), 302, 202, 201, 187, 172, 144.

UV (1% DMF in EtOH): $\lambda_{max}$363 nm ($\epsilon$=28,500), 313 nm ($\epsilon$=43,000).

EXAMPLE 35

Step 4—O-Deprotection; Step 5—Cyclization-1,2,8,8a-tetrahydro-7-methyl-[[5-benzyolamino-1H-indol-2-yl]carbonyl]cyclopropa[c]pyrrolo[3,2-e]indol-4(5H)-one To 160 mg (0.25 mmol) of the protected mesylate and 150 mg (1 mmol) of dry NaI under N$_2$ were added 6 ml of dry acetonitrile and 130 µl (1 mmol) of TMS-Cl. The mixture was heated to reflux for 15 min, cooled, diluted with ethyl acetate, and washed with 0.1M sodium thiosulfate. The organic phase was washed with water and brine and dried (Na$_2$SO$_4$). Triethylamine (400 µl) was added to the organic solution. After 30 min 200 µl of DMF was added and the solution was concentrated. The residue was chromatographed on silica gel, eluting with 50% acetone in cyclohexane containing 100 µl of triethylamine per 100 ml of eluent. The product-containing fractions were stripped, dissolved in 300 µl of acetone, and the light yellow particles which precipitated were washed with acetone and collected (10 mg).

NMR (DMSO-d$_6$): 11.85 (brs, 1H); 11.6 (brs, 1H); 10.33 (s, 1H); 8.27-8.03 (m, 3H); 7.7-7.5 (m, 5H); 7.27 (brs, 1H); 6.97 (brs, 1H); 6.77 (s, 1H); 4.5 (m, 2H); 3.15 (m, obscured by water peak); 2.03 (brs, 4H); 1.4 (m, 1H).

M.S. (F.A.B., glycerol+thioglycerol): 465 (M+H+H$_2$); 264, 202, 200, 187, 105.

UV (1% DMF in MeOH): $\lambda_{max}$364 ($\epsilon$=29,000), 308 ($\epsilon$=29,000).

EXAMPLE 36

Step 4—O-Deprotection; Step 5—Cyclization-1,2,8,8a-tetrahydro-7-methyl-2-[[5-benzyolamino-1H-indol-2-yl]carbonyl]cyclopropa[c]pyrrolo[3,2-e]indol-4(5H)-one To 102 mg (0.126 mmol) of the protected mesylate suspended in 7 ml of dry benzonitrile under N$_2$ were added 150 mg (1 mmol) of dry NaI and 130 µl (1 mmol) of TMS-Cl. The reaction was heated to ~60° for 50 min. It was cooled, diluted with ethyl acetate, and washed with 0.1M sodium thiosulfate, water and brine, and dried (Na$_2$SO$_4$). The concentrated residue, dissolved in 500 µl of DMF was chromatographed on silica gel, eluting with 50% acetone in cyclohexane.

The product-containing fractions also contained triethylammonium salt by NMR. They were dissolved in ethyl acetate and washed twice with water, then dried (Na$_2$SO$_4$) and stripped to 9.2 mg of a cream-colored solid.

NMR (DMSO-d$_6$): 11.9 (vbr, ~1H); 11.8 (vbr, ~1H); 11.65 (vbr, ~1H); 10.28 (brs, ~2H); 8.3–6.95 (m, ~14H); 6.75 (s, 1H); 4.52 (m, 2H); methine obscured by water peak; 2.02 (brs, 4H); 1.4 (m, 1H).

M.S. (F.A.B., glycerol): 623 (M+H+H$_2$); (F.A.B., glycerol+thioglycerol): 621 (M+H); 421, 199, 186, 105.

UV (MeOH): $\lambda_{max}$360 nm ($\epsilon$=27,500), 315 ($\epsilon$=39,000).

EXAMPLE 37

Step 4—O-Deprotection; Step 5—Cyclization-1,3,8,8a-tetrahydro-7-methyl-2-[[5-cyanoamino-1H-indol-2-yl]carbonyl]cyclopropa[c]pyrrole[3,2-e]indol-4(5H)-one To 63 mg (0.11 mmol) of the protected mesylate and 75 mg (0.5 mmol) of dry NaI in 3 ml of dry acetonitrile under N$_2$ was added 65 μl (0.5 mmol) of TMS-Cl. After heating to ~60° for 50 min, the reaction was cooled, diluted with ethyl acetate, and washed with 0.1M sodium thiosulfate and then brine, and dried (Na$_2$SO$_4$). Triethylamine (200 μl) was added and the solution was stored at 4° overnight. It was diluted with ethyl acetate, washed with water and brine and dried, and chromatogaphed on silica gel, eluting with 50% acetone in cyclohexane. The purest product fractions were concentrated to 6 mg of cream colored solid.

NMR (DMSO-d$_6$): 11.8 (brs, 1H); 11.5 (brs, 1H); 9.9 (brs, 1H); 7.55–6.9 (m, 5–6H); 6.7 (s, 1H); 4.47 (m, 2H); 3.2 (m, obscured by water peak); 2.0 (brs, 4H); 1.38 (m, 1H).

M.S. (F.A.B., glycerol+thioglycerol): 384 (M+H); 269, 257, 199, 195, 184, 177.

UV (1% DMSO in MeOH): $\lambda_{max}$357 nm ($\epsilon$=15,500); 310, 295 nm ($\epsilon$=16,700).

EXAMPLE 38

Step 4—O-Deprotection; Step 5—Cyclization-1,2,8,8a-tetrahydro-7-methyl-2-[[5-ureido-1H-indol-2-yl]carbonyl]cyclopropa[c]pyrrolo[3,2-e]indol-4(5H)-one To 56 mg (0.095 mmol) of the protected mesylate in 3 ml of benzonitrile under N$_2$ were added 150 mg (1 mmol) of NaI and 130 μl (1 mmol) of TMS-Cl. The suspension was heated to ~70° for 30 min, then cooled. It was diluted with ethyl acetate and washed with 0.1M sodium thiosulfate, water, and brine, and dried (Na$_2$SO$_4$). The residue was chromatographed on silica gel, eluting with 70% acetone in cyclohexane. The fractions containing the product and its uncyclized precursor were concentrated, dissolved in 0.5 ml of acetone, and treated with 10 μl of triethylamine. The light yellow particles which precipitated were washed and collected (2.7 mg). A second crop of 6.7 mg was also obtained, but the extinction coefficient was 25% lower.

NMR (DMSO-d$_6$): 11.6 (vbr, ~1H); 11.52 (vbr, ~1H); 8.5 (brs, 1H); 7.86–6.9 (m, ~5H); 6.71 (s, 1H); 5.75 (brs, 2H); 4.48 (m, 2H); methine obscured by water peak; 2.0 (brs, 4H); 1.35 (m, 1H).

M.S. (F.A.B., glycerol+thioglycerol): 402 (M+H); 200, 199, 149.

UV (1% DMSO in MeOH): $\lambda_{max}$362 nm ($\epsilon$=15,000); 310 nm ($\epsilon$=15,000).

EXAMPLE 39

Step 4—O-Deprotection; Step 5—Cyclization-1,2,8,8a-tetrahydro-7-methyl-2-[[5-[[[5-ureido-1H-indol-2-yl]carbonyl]amino]-1H-indol-2-yl]carbonyl]cyclopropa[c]pyrrolo[3,2-e]indol-4(5H)-one To 39 mg (0.052 mmol) of the protected mesylate in 3 ml of dry benzonitrile under N$_2$ were added 100 mg (0.66 mmol) of NaI and 85 μl (0.66 mmol) of TMS-Cl. The mixture was heated to 80° for 30 min, then cooled and diluted with ethyl acetate. The organic phase was washed with 0.1M sodium thiosulfate and then brine, and dried (Na$_2$SO$_4$). Triethylamine (50 μl) was added, causing instant clouding of the solution. This was concentrated and chromatographed on silica gel, adding a small amount of DMSO and 50 μl triethylamine before placing on the column. Elution with 70% acetone in cyclohexane removed non-polar components. The product was eluted with acetone. The product fractions were concentrated to 3 mg of a cream colored solid.

NMR (DMSO-d$_6$): 11.8 (vbr, ~1H); 11.55 (vbr, ~2H); 10.2 (brs, 1H); 8.4 (brs, 1H); 8.26 (brs, 1H); 7.83 (brs, 1H); 7.65–7.1 (m, ~6H); 6.95 (m, 1H); 6.75 (s, 1H); 5.72 (brs, 2H); 4.53 (m, 2H); methine obscured by water peak; 2.0 (brs, 4H); 1.4 (m, 1H).

M.S. (F.A.B., glycerol+thioglycerol): 560 (M+H); 274, 232, 216, 199, 197.

UV (1% DMSO in MeOH): $\lambda_{max}$360 nm ($\epsilon$=29,000); 312 nm ($\epsilon$=40,000).

EXAMPLE 40

Step 4—O-Deprotection; Step 5—Cyclization-Cyclopropa[c]pyrrolo[3,2-e]indol-4(5H)-one, 1,2,8,8a-tetrahydro-7-methyl-2-(2-quinolinylcarbonyl)-

A 286 mg (0.52 mmol) quantity benzyl ether and 353 mg (2.4 mmol) dry sodium iodide was stirred under N$_2$ in 8 ml acetonitrile. Syringed in 288 μl (2.27 mmol) trimethylsilyl chloride. Refluxed for 30 min, TLC after 20 minutes showing no starting material left. The reaction mixture was cooled to RT and partitioned between EtOAc-2% sodium thiosulfate solution. The organic phase was dried over Na$_2$SO$_4$ and treated with 900 μl triethylamine for 30 minutes, followed by evaporation under vacuum.

The crude product was chromatographed over 30 g silica gel, eluting with 300 ml 50% acetone-50% hexane-0.5% NEt$_3$ and 300 ml 60% acetone-40% hexane-0.5% NEt$_3$. Fractions of 10 ml were collected, analyzing them by TLC. The major product spot was found in fractions 19–40, which upon combining and evaporating left a very insoluble tan solid weighing 81 mg (44% yield).

TLC: Silica gel; UV visualization; 50% acetone-50% hexane-0.5% NEt$_3$; R$_f$: 0.42.

M.S.: M+found: 355.1298; calculated for C$_{22}$H$_{17}$N$_3$O$_2$: 355.1321. Other ions assigned: 327, 326, 228, 213, 199, 128.

NMR (d$_6$-DMSO, TMS, δ): 1.45 (m, 1H); 1.96 (m, 1H); 2.0 (s, 3H); 3.1–3.3 (broad, 1H); 4.3–4.5 (m, 2H); 6.9 (s, 1H); 7.8–8.2 (m, 6H); 8.6–8.8 (d, 1H).

UV (0.01M phosphate, pH 7.2): A$_{357}$=0.493; $\epsilon_{max}$=11,700.

EXAMPLE 41

Step—O-Deprotection; Step 5—Cyclization-Cyclopropa[c]pyrrolo[3,2-e]indol-4(5H)-one, 1,2,8,8a-tetrahydro-7-methyl-2-(2-pyrrolylcarbonyl)-

A 0.19 mmol quantity crude benzyl ether and 131 mg (0.88 mmol) of dry sodium iodide were stirred under $N_2$ in 3 ml acetonitrile. Syringed in 107 µl (0.84 mmol) trimethylsilyl chloride and refluxed for 30 minutes. TLC after 25 minutes reaction had shown no starting material left. The reaction mixture was cooled to room temperature and partitioned between EtOAc-2% sodium thiosulfate. The organic layer was dried over $Na_2SO_4$ and treated with 200 µl $NEt_3$ for 30 minutes, followed by evaporation under vacuum. The crude product was chromatographed over 15 g. silica gel, eluting with 50% acetone-50% hexane-0.2% $NEt_3$. Fractions of 10 ml. were collected, analyzing them by TLC. Fractions 20–37 contained the product which shows up very bright under long wave length UV and were combined and evaporated. A 42 mg. residue was obtained which by NMR still contained a considerable amount of $NEt_3$. Crystallization from acetone gave Group 1 (1.4 mg.) and Group 2 (9.0 mg.).

The mother liquors were rechromatographed over 3 g silica gel, eluting with 50% acetone-50% hexane-0.2% $NEt_3$, followed by 75% acetone-25% hexane-0.2% $NEt_3$ when the product seemed to drop off. Fractions of 0.5 ml were collected, analyzing them by TLC. The product was found in fractions 11–67 which were combined and evaporated. Crystallization from acetone gave Group 3 (1.2 mg) which was combined with Groups 1 and 2.

TLC: Silica gel; UV visualization; 50% acetone-50% hexane-0.2% $NEt_3$; $R_f$: 0.27.

NMR ($d_6$-acetone, TMS, δ): 1.25–1.5 [m, 3H (includes $ET_3NH+X-$)]; 2.3–2.45 (d, 3H); 3.15–3.75 [m, 3H (includes $ET_3NH+X-$)]; 4.4–4.6 (m, 1H); 6.2–6.35 (broad, 1H); 6.75–6.9 (broad, 1H); 6.95–7.1 (broad, 2H); 7.6 (s, 1H).

M.S.: M+found: 293.1175; calculated for $C_{17}H_{15}N_3O_2$: 293.1164; other major assigned ion at 200.

| UV (0.01 M phosphate, pH 7.2): | $\lambda_{max}$ | A | $\epsilon_{max}$ |
|---|---|---|---|
| | 310 shoulder | 0.440 | 10,350 |
| | 368 | 0.455 | 10,700 |

EXAMPLE 42

To a solution of the N-benzoyl cyclopropylspirodienone (estimated <10 mg) in 5 ml of methanol and 5 ml of water was added 2 ml of 40% $CH_3NH_2$ in water. The mixture was stirred for 1 hr at 25°, then concentrated and worked up with aqueous $NH_4Cl$ and $CH_2Cl_2$. The organic phase was dried ($Na_2SO_4$), concentrated, and chromatographed on silica gel, eluting with 10% methanol/$CHCl_3$, to afford about 4 mg of a light tan solid.

NMR (DMF-$d_7$): 7.05 (br, 1H); 6.75 (m, 1H); 5.28 (s, 1H); 3.83.

EXAMPLE 43

Steps 7 and 8—Resolution of diastereomers (Chart III)

Step A—To 1.5 g. (3.89 mmol) of 1,2,3,6-tetrahydro-8-(methyl)-3-(methylsulfonyl)-5-(phenylmethoxy)-[1,2-6:4,3-b']dipyrrole-1-methanol (see Chart III) in 60 ml. of methylene chloride was added 1.2 g. (3.95 mmol) of N-t-butoxycarbonyl-L-trypotphan, 0.77 g. (4.0 mmol) of ethyldimethylaminopropyl carbodiimide (HCl salt), and 0.08 g. (0.65 mmol) of 4-dimethylaminypyridine to form the racemic tryptophan ester. The mixture was stirred, under a nitrogen atmosphere, at room temperature for two days. It was then diluted with methylene chloride and extracted with 0.5% aqueous acetic acid, followed by saturated sodium chloride. The yellow solution was dried over $Na_2SO_4$ and evaporated to 2.7 g. of yellow solid. The solid was dissolved in 10 ml. of tetrahydrofuran and 10 ml. of hexane was added to induce crystallization. Two further recrystallizations from tetrahydrofuran and hexane afforded crystals of >99% diastereomeric purity in 58% of theoretical yield. Diastereomeric purity was determined by high pressure liquid chromatography on silica gel, eluting with 27% tetrahydrofuran in hexane, which gave baseline separation of the isomers.

NMR (CDCl$_3$): 8.4 (brs, 1H), 8.32 (brs, 1H), 7.7–7.0 (m, ~12H), 5.22 (S, 2H), 5.1 (br, 1H), 4.7 (m, 1H), 4.35 (m, 1H), 3.9–3.2 (m, 6H), 2.7 (s, 3H), 2.4 (S, 3H), 1.5 (s, 9H).

Step B: To 1.1 g. (1.64 mmol) of the desired N-t-BOC-L-tryptophan ester from Step A in 20 ml. of tetrahydrofuran and 20 ml. of methanol under nitrogen was added, with stirring, 12 ml. of 1M aqueous sodium hydroxide to cleave the ester. After 1 hour at 20° C., the organic solvents were evaporated and the aqueous phase was extracted twice with ethyl acetate. The organic phase was washed once with 10% sodium bicarbonate and once with saturated NaCl, and dried over $NA_2SO_4$. Solvent evaporation afforded 0.57 g. (1.48 mmol, 90%) of a slightly yellow foam, whose NMR spectrum matched that of the starting material in Example 43.

NMR (acetone-$d_6$): 10.2 (brs 1H), 7.65–7.35 (m, 5H), 7.1 (nm, 2H), 5.26 (S, 2H), 4.3–3.45 (m, ~5H), 2.82 (s, 3H), 2.4 (s, 3H).

Step C: When synthesis steps 1–5, described hereinabove, are carried out on this substance from Step B exactly as described in Examples 1, 7, 19 and 34, the product obtained is U-71,184, whose circular dichroism spectrum (methanol) exhibits peaks at 335 and 285 nm, and a trough at 315 nm, and whose non-chiral spectroscopic properties are identical to those of the racemate, U-68,415.

Examples 44 through 50, shown in Chart IV are illustrative of the steps in the process of preparing compounds wherein $R_5$ is the dimer combination xvii+xvii bound together with the amide linkage. The specific compound prepared is (7bR,8aS)-1,2,8,8a-tetrahydro-7-methyl-2-[[5-(((2H-benzofuran-2-yl)carbonyl)-amino)-1H-indol-2-yl]carbonyl]cyclopropa]pyrrolo[3,2-e]indol-4(5H)-one (U-73,975).

EXAMPLE 44

Step 1

Benzofuran-2-carboxylic acid (coumarilic acid, 1.5 mmol), described by R. Fittig, Ann., Vol. 216, 162 (1883), and 1-ethyl-3-(3-dimethylaminopropyl)carbodiimide hydrochloride (EDC, 1.64 mmol) were treated with 2.4 ml of a 0.6M solution of ethyl 5-amino-indole-2-carboxy-late, described by M. A. Warpehoski, Tet. Lett., Vol. 27 No. 24, (1986), pages 2735–2738, (which amino-ester is also referred to in footnote 11 of a paper by M. A. Warpehoski in Tetrahedron Letters, 27, No. 35, pages 4102–4106 (1986)) in dimethylformamide (DMF). The reaction was stirred under a nitrogen atmosphere for 40 hours and then diluted with ethyl acetate and water. The layers were separated and organic layer was washed with aqueous sodium bicarbonate, aqueous sodium bisulfate, and with brine, and then was dried over anhydrous sodium sulfate, and filtered. Removal of the solvent under reduced pressure afforded the crude product of Step 1. The crude product was chromatographed on silica gel eluting with 9:1 methylene chloride-acetone to give a 90% yield of pure product of Step 1. NMR (pyridine-d5, TMS): 1.20 (t,3H); 4.40 (q,2H); 7.20 top 7.95 (m,6H); 8.10 (d,1H); 8.20 (d,1H); 8.75 (s,1H); 8.81 (d,1H); 11.2 (s,1H) MS(FAB); Calc. for $C_{20}H_{16}N_2O_4$: 348.1110; Found: 348.1147; m/z 302,145,89; TLC (silica gel): $R_f$=0.18 in (25–75)ethyl acetate-hexane.

EXAMPLE 45

Step 2

A solution of 0.29 mmol of the ester product of Step 1 in 4 ml of pyridine was treated with 0.4 ml of 1N aqueous sodium hydroxide solution, stirred for two days at room temperature, and quenched with 0.4 ml 1N aqueous hydrochloric acid. The resulting solution was partitioned between brine and tetrahydrofuran. The layers were separated and the organic layer dried over sodium sulfate and filtered. The solvents were removed in vacuo to give a quantitative yield of the crude product of Step 2 which was used without further purification. NMR (pyridine-d5,TMS): 7.15–7.95 (m,7H); 8.05–8.25 (dd,1H); 8.7–8.95 (m,1H); 9.1 (s,1H); 11.1 (s,1H); 13.2 (s,1H).

EXAMPLE 46

Step 3

Optically active n-mesylindoloindole (1,2,3,6-tetrahydro-8-(methyl)-3-(methylsulfonyl)-5-(phenylmethoxy)-[1,2-b:4,3-b']dipyrrole-1-methanol, 0.52 mmol, was dissolved in 20 ml of dimethoxyethane, treated under a nitrogen atmosphere dropwise with 1.1 ml of Red-A1 (3.4M solution of bis(2-methoxy-ethoxy)aluminum hydride in toluene), heated at reflux for one hour, cooled to 0° C., and carefully quenched with 15% aqueous potassium carbonate. Using only nitrogen-purged solvents, the mixture was diluted with ether and water. The aqueous layer was re-extracted, and the combined ether layers were dried over anhydrous sodium sulfate, filtered and evaporated. The resulting crude oil was re-evaporated with toluene to give an air sensitive brown solid amine.

A solution of a total of 0.6 mmol of this amine in 2.3 ml of DMF and 0.6 mmol of EDC was added to a solution of 0.6 mmol of the acid product of Step 2 in 10 ml of DMF. The resulting solution was stirred at room temperature for three days. The reaction mixture was diluted with methylene chloride and washed with 5% sodium bisulfate, 5% sodium bicarbonate and brine. The aqueous layers were back-extracted with methylene chloride. The organic layers were combined, dried over sodium sulfate and evaporated.

Crystallization from pyridine and methylene chloride afforded a 59% yield of the product of Step 3. NMR(acetone-d6,TMS): 2.4 (s,3H); 3.2–5.2 (m,6H); 5.1 (s,3H); 6.8–7.9 (m,14H); 8.2 (s,1H); 8.45 (s,1HO: 9.8 (s,1H); 10.2 (s,1H); 11.25 (s,1H). MS (FAB): Calc. for $C_{37}H_{30}N_4O_5$: 610.2216; Found: 610.2209; m/z 687, 611,579,520,519,489,303, 277, 218, 187, 145; TLC (silica gel): $R_f$=0.25 in (50-50) ethyl acetate-hexane.

EXAMPLE 47

Step 4

The starting alcohol (product of Step 3, 0.48 mmol) dissolved in pyridine (5 ml) was cooled in an ice bath and put under a nitrogen atmosphere. Methanesulfonyl chloride (169 μl, 2.18 mmol) was syringed into the reaction flask. Stirring at room temperature for 5–6 hours brought the reaction to completion. The reaction mixture was partitioned between ethyl acetate and 1N aqueous hydrochloric acid. The organic fraction was washed with brine, dried over anhydrous sodium sulfate, and filtered. The solvents were removed in vacuo to give essentially a quantitative yield of the crude product of Step 4. NMR (acetone-d6,TMS): 2.4 (s,3H); 2.95 (s,3H); 3.9–5.3 (m,5H); 5.13 (s,2H); 6.9–7.9 (m,13H); 8.15 (s,1H); 8.5 (S,1H); 8.75 (d,1H); 9.9 (s,1H); 10.4 (d,1H); 11.25 (s,1H). TLC (silica gel): $R_f$=0.57 in (50-50) ethyl acetate-hexane.

EXAMPLE 48

Step 5

A solution of the crude product of Step 4 (approx. 0.48 mmol) in 5 ml. of DMF under a nitrogen atmosphere was treated with 55 mg of lithium chloride, heated at 75° C. for 2 hours, cooled to room temperature, and partitioned between ethyl acetate and 1:1 brine-water. The organic layers were washed with brine, dried over anhydrous sodium sulfate, and filtered. The solvent was removed under reduced pressure and the residue chromotographed on silica gel eluting with 40% ethyl acetate in hexane to give a 64% yield of the pure product of Step 5. NMR (CDCl3, TMS): 2.50 (d,3H); 3.49 (t,1H); 3.94 (dd,1H); 4.13 (t,1H); 4.67 (m,1H); 4.90 (dd,1H); 5.30 (d,2H); 7.04 (m,1H); 7.13 (d,1H); 7.33–7.83 (m,13H); 8.10 (s,1H); 8.34 (s,1H); 8.47 (s,1H); 9.65 (s,1H); $^{13}$CNMR (CDCl3,TMS): 11.254, 43.263, 46.989, 55.014, 70.317, 95.515, 105.971, 110.525, 110,979, 111.646, 112.007, 113.462, 114.063, 119.031, 122,690, 123,170, 123.718, 123.851, 123.213, 126.949, 127.684, 127.924(2), 128.084, 128.165, 128.458(2), 130.368, 131.650, 133.079, 136.551, 136.858, 145.137, 148.676, 154.658, 156.461, 159.559; MS(FAB): Calc. for $C_{37}H_{29}Cl_1N_4O_4$: 628.1877; Found: 628.1896; m/z 629, 579, 537, 393, 327, 326, 303, 277, 236, 235, 199, 187, 145, 91; TLC (silica gel): $R_f$=0.69 in (50-50) ethyl acetate-hexane.

EXAMPLE 49

Step 6

A solution of the product of Step 5 (0.26 mmol) in 4 ml of tetrahydrofuran and 2 ml of methanol at 0° C. was treated with 2.6 mmol of ammonium formate and 0.16 g of 10% palladium on charcoal, stirred at 0° C. for 30 minutes, filtered through celite and diluted with ethyl acetate. The ethyl acetate solution was washed with water and brine, dried over anhydrous sodium sulfate, and filtered. The solvents were removed in vacuo to give the product of Step 6 in 95% yield. NMR (DMF-d7,TMS): 2.432 (d,3H); 3.61–3.75 (dd,1H); 3.92–4.04 (dd,1H); 4.04–4.19 (m,1H); 4.67–4.84 (m,2H); 7.15–7.90 (m,9H); 8.42 (d,1H); 9.87 (s,1H); 10.55 (s,1H); 10.75 (d,1H); 11.66 (s,1H); MS(FAB): Calc. for $C_{30}H_{24}Cl_1N_4O_4$: 539.1486; Found: 539.1484; m/z 538, 505, 489, 303, 237, 236, 235, 201, 187, 145; UV (EtOH): $\lambda_{max}$=209 ($\epsilon$=42950), 219 ($\epsilon$=39300), 346 ($\epsilon$=26300); TLC (silica gel): $R_f$=0.09 in (50-50) ethyl acetate-hexane.

EXAMPLE 50

Step 7

A solution of the product of Step 6 (0.19 mmol) in 5 ml acetonitrile, 4 ml of triethylamine, and 16 ml of water was stirred for 30 minutes at room temperature and then cooled 0° C. The resulting solid which precipitated during the course of the reaction was collected by vacuum filtration and dried in vacuo to give an 80% yield of pure (7bR,8αS)-1,2,8,8α-tetrahydro-7-methyl-2-[[5-(((2H-benzofuran-2-yl)carbonyl-amino)-1H-indol-2-yl]carbonyl]cyclopropa]pyrrolo[3,2-e]indol-4(5H)-one (U-73,975). NMR (DMF-d7,TMS): 1.49–1.54 (t,1H); 2.04–2.10 (m,1H); 2.102 (s,3H); 3.24-3.31 (m,1H); 4.57-4.72 (m,2H); 6.84 (s,1H); 7.03 (d,1H); 7.32 (d,1H); 7.39-7.92 (m,7H); 8.46 (d,1H); 10.60 (s,1H); 11.57 (s,1H); 11.83 (s,1H). MS (FAB): Calc. for $C_{30}H_{23}N_4O_4$: 503.1719; Found: 503.1742; m/z 303, 201, 199, 187, 145; UV (EtOH): $\lambda_{max}$=2.10 ($\epsilon$=39700), 312 ($\epsilon$=37440), 365 ($\epsilon$=31110); TLC (silica gel): $R_f$=0.22 in (40-60) acetone-hexane.

Many of the compounds of the subject invention have useful cytotoxic activity against murine L1210 tumor cells in suspension, which is a standard model for such tests before the compounds are tested in humans. If a compound is active against such tumor cells, then it presumptively will have activity against tumor cells in other animals and humans. Following is a table showing the results of testing various compounds against L1210 in suspension using standard, well-known procedures. The compounds are identified by an internal designation called a "U-" number. The structural identify of the "U-" numbered compounds is shown in Chart I.

| Compound | L-1210 (3-Day Cell Growth) | |
|---|---|---|
| | $ID_{50}$ µg/ml | $ID_{90}$ µg/ml |
| U-62,736 | 0.039 | 0.18 |
| U-66,777 | 0.18 | 0.92 |
| U-66,866 | 0.0015 | 0.0045 |
| U-68,880 | 0.0000080 | 0.000019 |
| U-68,415 | 0.000018 | 0.000044 |
| U-68,819 | 0.00048 | 0.0015 |
| U-66,694 | 0.00015 | 0.00034 |
| U-67,785 | 0.000072 | 0.00019 |
| U-67,786 | 0.000046 | 0.00010 |
| U-68,749 | 0.0034 | 0.0084 |
| U-68,846 | 0.000034 | 0.000096 |
| U-66,664 | 0.0048 | 0.018 |
| U-66,665 | 0.0090 | 0.032 |

Examples of compounds of the subject invention demonstrate antitumor activity in P388 leukemic mice, and also show significant activity in the L1210 leukemia and B16 melanema murine test systems. These murine test systems are predictive for clinically useful human antitumor agents (see, for example, A. Geldin, J. M. Vendetti, J. S. MacDonald, F. M. Muggia, J. E. Henney and V. T. DeVita, European J. Cancer, Vol. 17, pp. 129-142, 1981; J. M. Vendetti, Cancer Treatment Reports, Vol. 67, pp. 767-772, 1983; and J. M. Vendetti, R. A. Wesley, and J. Plowman, Advances in Pharmacology and Chemotherapy, Vol. 20, pp. 1-20, 1984), and it is therefore presumed that the compounds of the subject invention will be useful in the control and treatment of cancer in humans when given, for example, intravenously in doses of 0.001 to about 10 mg. per kg. of body weight per day, the exact dose depending on the age, weight and condition of the patient, and on the frequency of administration. Following is a table showing the results of testing various compounds intraperitoneally against P388 leukemic mice using standard well-known procedures (In Vivo cancer, Models, NIH Publication No. 84-2635, 1984). The structural identify of the "U-" numbered compounds is shown in Chart I. In the table % ILS refers to percent increase in life span of treated animals over controls.

| Compound | P388 % ILS | |
|---|---|---|
| U-66,866 | 71 | (at 12 mg./kg.) |
| U-68,880 | 71 | (at 0.10 mg./kg.) |
| U-68,415 | 4/6 | cures (at 0.05 mg./kg.) |
| U-68,819 | 71 | (at 1 mg./kg.) |
| U-66,694 | 164 | (at 0.63 mg./kg.) |
| U-63,749 | 113 | (at 6 mg./kg.) |
| U-68,846 | 82 | (at 0.05 mg./kg.) |
| U-69,059 | 4/6 | cures (at 0.5 mg./kg.) |
| U-67,785 | 60 | (at 0.06 mg./kg.) |
| U-69,058 | 96 | (at 0.50 mg./kg.) |
| U-69,060 | 138 | (at 0.10 mg./kg.) |

The compound U-73,975, a compound wherein $R_5$ is the dimer combination xvii and xvii bound together with the amide linkage, has exhibited particularly good activity against solid tumors as well as having shown good solubility and stability characteristics in aqueous solution. For example, in B16 melanoma implanted subcutaneously in mice, a 61% increase in life span over control (non-drug treated) animals was observed with a single intravenous dose of U-73,975 significantly increased the lifespan of mice implanted with M5076 ovarian sarcoma and Lewis lung carcinoma. U-73,975 also significantly inhibited the growth of a human lung tumor (Lx-1 carcinoma) xenograph in nude mice. These characteristics are advantageous for antitumor agents.

All the compounds of the subject invention have UV absorption in the range of 250 nm to 380 nm. Thus, novel compounds of the subject invention are useful as UV absorbents in technical and industrial areas, as follows:

(a) textile materials, for example, wool, silk, cotton, hemp, flax, linen and the like; and (b) natural or synthetic resins.

Depending on the nature of the material to be treated, the requirements with regard to the degree of activity and durability, and other factors, the proportion of the light screening agent to be incorporated into the material may vary within fairly wide limits, for example, from about 0.01% to about 10%, and, advantageously, 0.1% to 2% of the weight of the material which is to be directly protected against the action of UV rays.

The compounds of this invention have anti-microbial activity and hence are useful as anti-bacterialagents. For example, compounds 5 (U-66,665) and 6 (U-66,694) have activity against the following microorganisms:

*Bacillus subtilis, Klebsiella pneumonia, Sarcina lutea, Escherichia coli, Proteus vulgaris, Staphylococcus aureus, Salmonella schottmeulerri, Mycobacterium avium, Saccharomyces pastorianus,* and *Penicillium oxalicum* and compound U-73,975 has activity against *Escherichia coli, Klebsiella pneumonia,* and *Staphyloccocus areus.* Compounds 5 are those obtained from Step 4 in Charts I and II, illustratively U-66,665. Compounds 6 are those obtained from Step 5 in Charts I and II, illustratively U-66,694.

Thus, these compounds are useful to control the proliferation of these microbes in various environments using standard microbiological techniques. Such environments include laboratory benches in a microbiological laboratory which can be cleansed with a formulation of the above compounds; dental utensils contaminated with *S. aureus*, and the like.

In a manner analogous to that of Examples 2–13 the following carboxylic acids may be coupled to the pyrroloindole product formed in Example 1. Mesylation of these coupled products in like manner to Examples 14–25, followed by deprotection and ring closure as described for Examples 26–41, will provide the structures indicated and named.

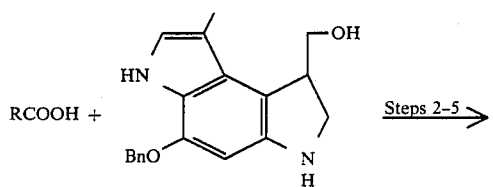

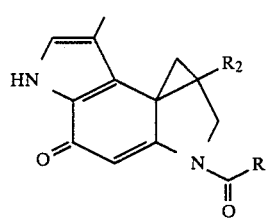

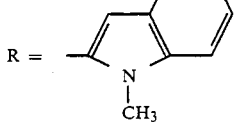

R =

Cyclopropa[c]pyrrol[3,2-e]indol-4(5H)-one, 1,2,8,8a-tetrahydro-2-(1-methylindol-2-ylcarbonyl)-7-methyl-

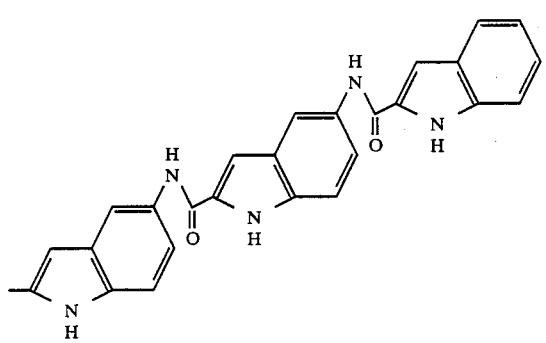

Cyclopropa[c]pyrrolo[3,2-e]indol-4-(5H)-one, 1,2,8,8a-tetrahydro-2-[[5-[[[5-[(1H-indol-2-ylcarbonyl)amino]-1H-indol-2-yl]carbonyl]amino]-1H-indol-2-yl-carbonyl]-7-methyl-

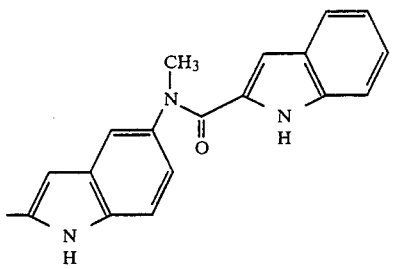

Cyclopropa[c]pyrrolo[3,2-e]indol-4[5H]-one, 1,2,8,8a-tetrahydro-2-[[5-[(1H)-indol-2-ylcarbonyl)methylamino]-1H-indol-2-yl]carbonyl]-7-methyl-

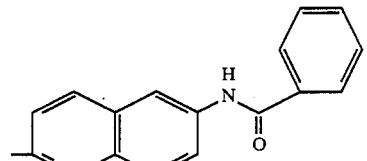

Cyclopropa[c]pyrrolo[3,2-e]indol-4-(5H)-one, 1,2,8,8a-tetrahydro-2-[[6-benzoyl-amino)-quinolin-2-yl]carbonyl]-7-methyl-

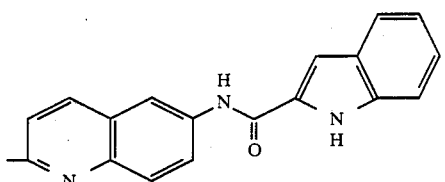

Cyclopropa[c]pyrrolo[3,2-e]indol-4(5H)-one, 1,2,8,8a-tetrahydro-2-[[6-[(1H)-indol-2-ylcarbonyl)amino]-quinolin-2-yl]carbonyl]-7-methyl-

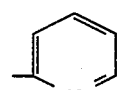

Cyclopropa[c]pyrrolo[3,2-e]indol-4-(5H)-one, 1,2,8,8a-tetrahydro-2-(picolinyl-2-yl)carbonyl-7-methyl-

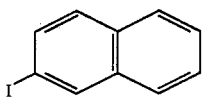

Cyclopropa[c]pyrrolo[3,2-e]indol-4(5H)-one, 1,2,8,8a-tetrahydro-2-7-methyl-2-(2-naphthaleneylcarbonyl)-

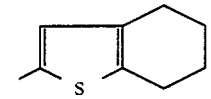

Cyclopropa[c]pyrrolo[3,2-]indol-4(5H)-one, 1,2,8,8a-tetrahydro-2-(1H)-benzothiophen-2-ylcarbonyl)-7-methyl-

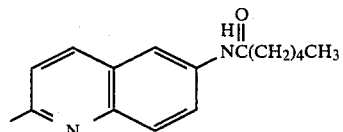

Cyclopropa[c]pyrrolo[3,2-e]indol-4(5H)-one, 1,2,8,8a-tetrahydro-2[[6-hexanoylamino-quinolin-2-yl]carbonyl]-7-methyl-

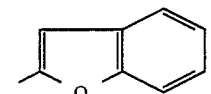

Cyclopropa[c]pyrrolo[3,2-e]indol-4(5H)-one, 1,2,8,8a-tetrahydro-2-(1H)-benzofuran-2-yl-carbonyl)-7-methyl -continued
/(CH₂)₄CH₃
-continued
Cyclopropa[c]pyrrolo[3,2-e]indol-4(5H)-one, 1,2,8,8a-tetrahydro-2-heaxnoyl-7-methyl-
GENERAL FORMULAE CHART
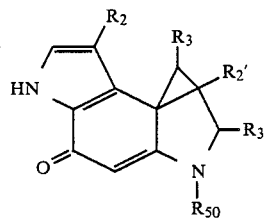
I
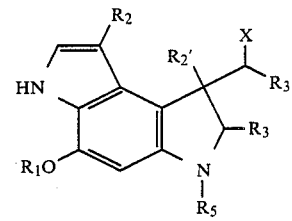
II
RING NUMBERING SYSTEM FOR FORMULA (I) AND (II) COMPOUNDS
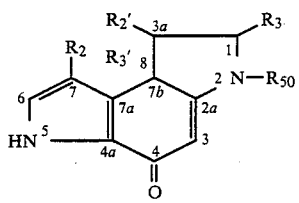
A
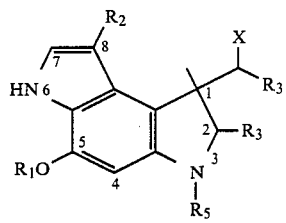
B
SPECIES COMPOUND FORMULA CHART
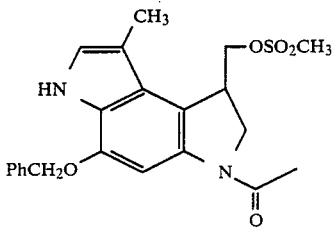
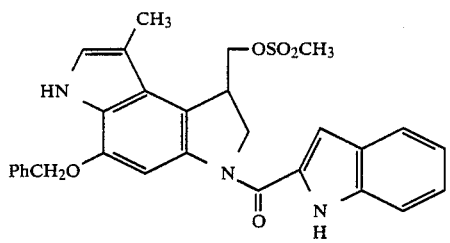
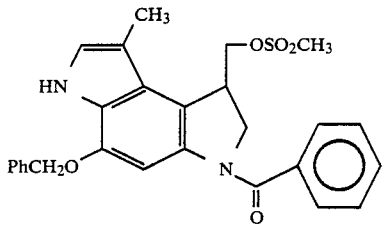

-continued
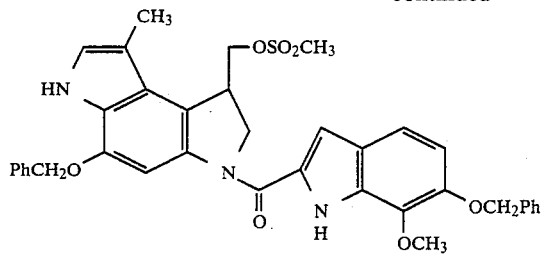
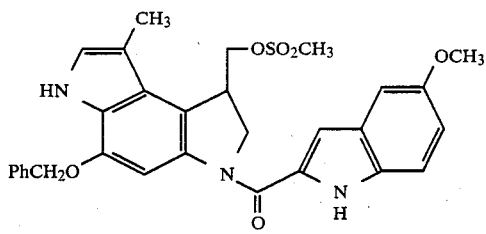
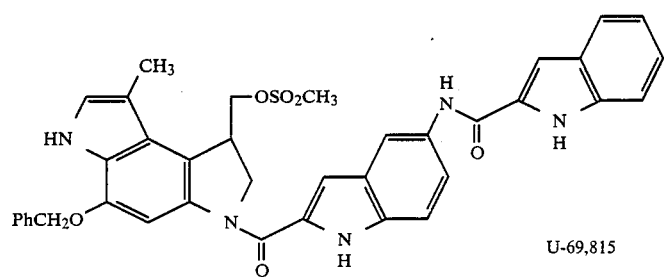
U-69,815
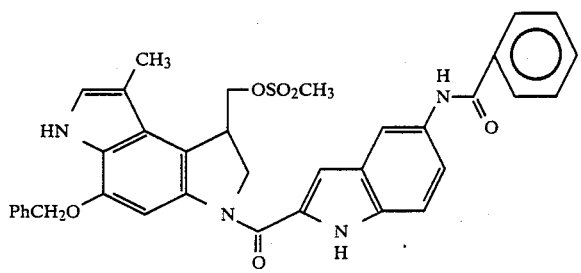
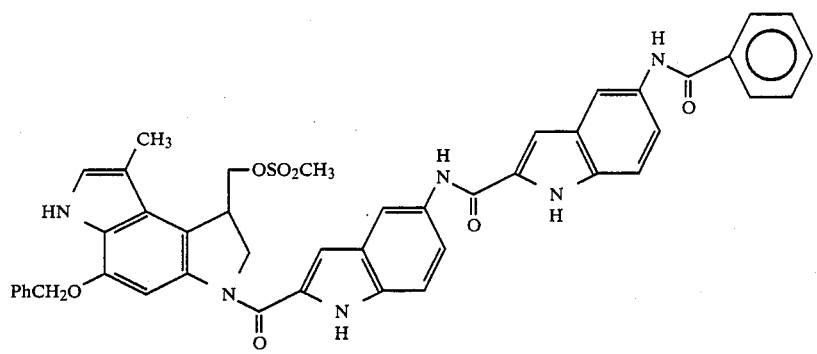
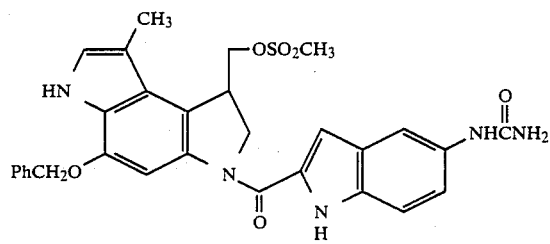

-continued
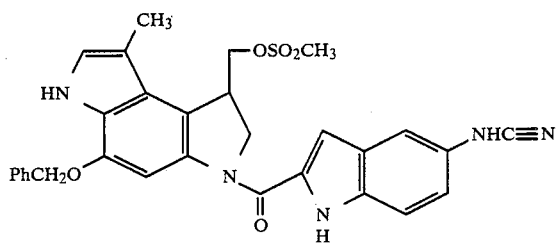
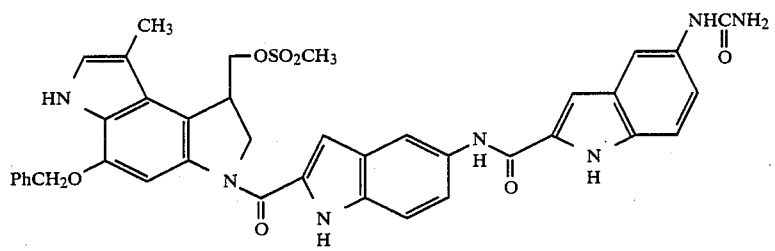
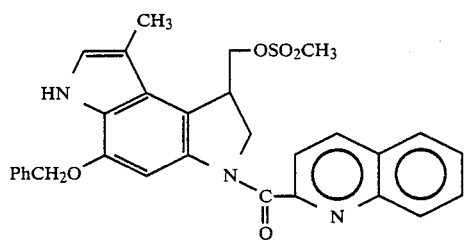
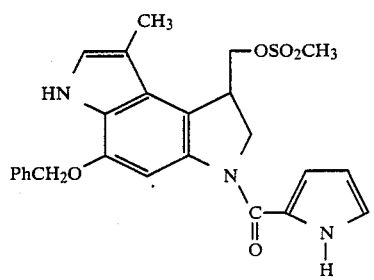
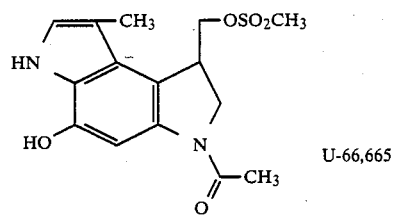
U-66,665
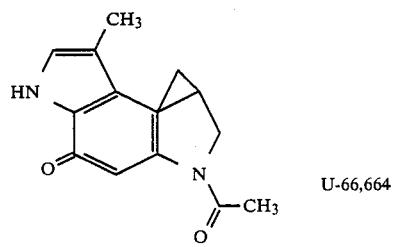
U-66,664

-continued
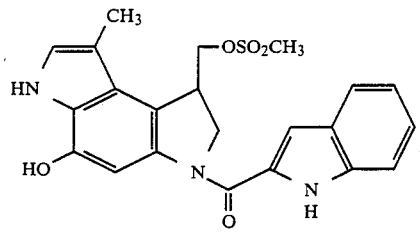
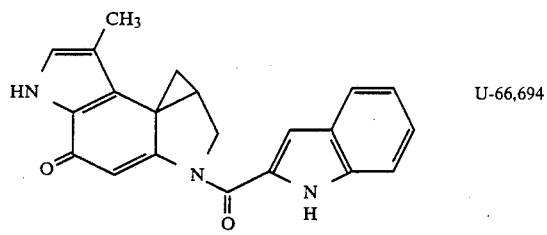
U-66,694
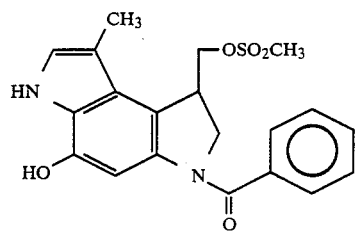
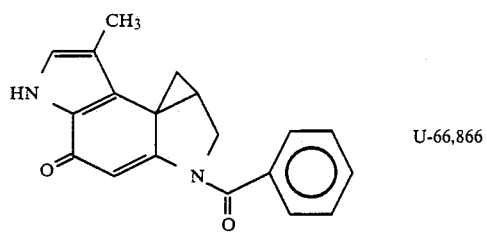
U-66,866
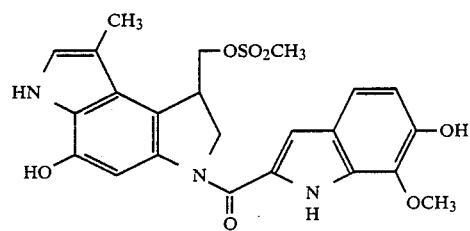
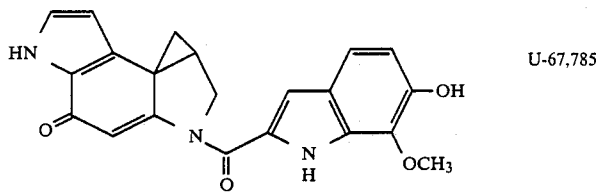
U-67,785
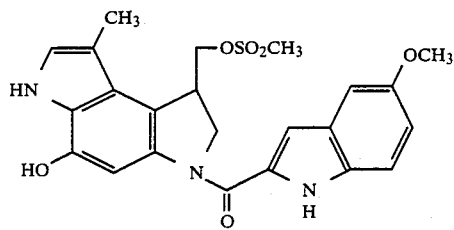

-continued
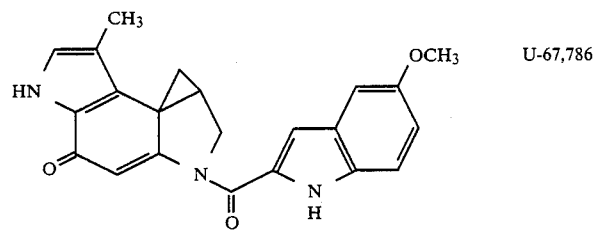
U-67,786
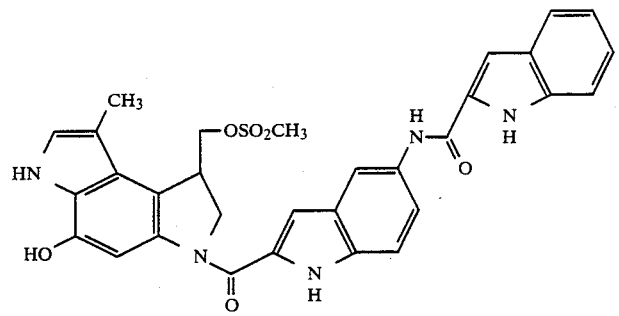
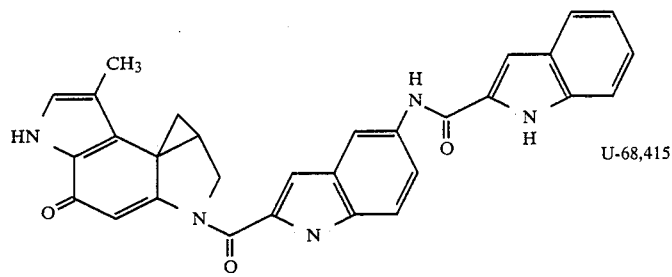
U-68,415
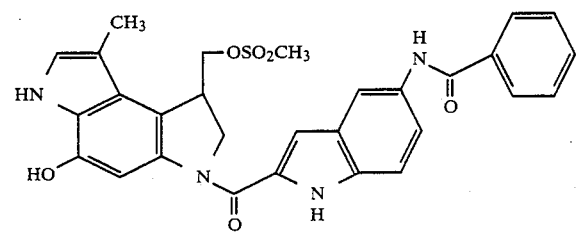
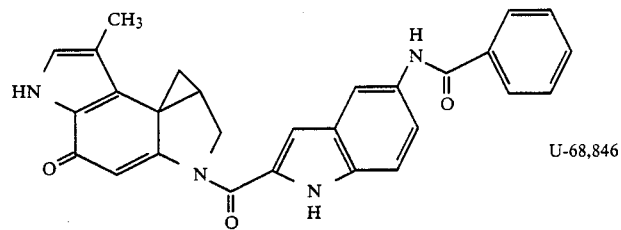
U-68,846
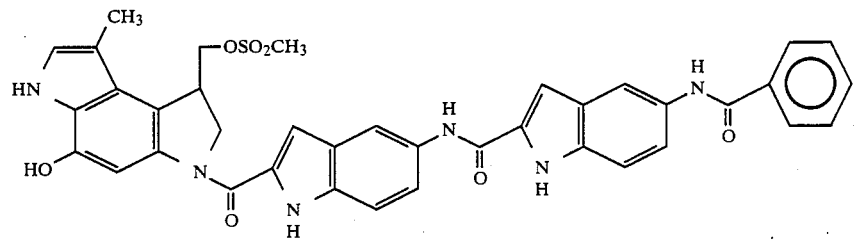

-continued
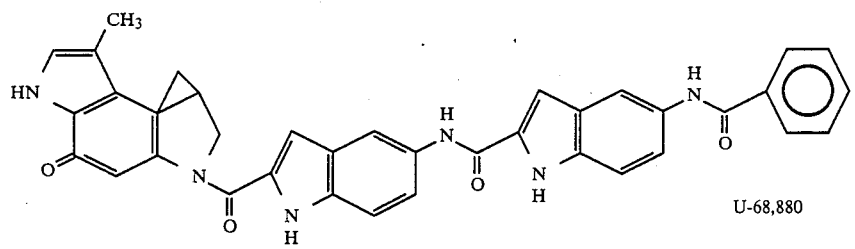
U-68,880
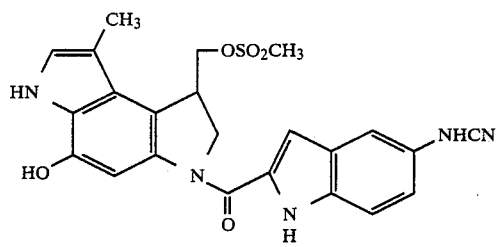
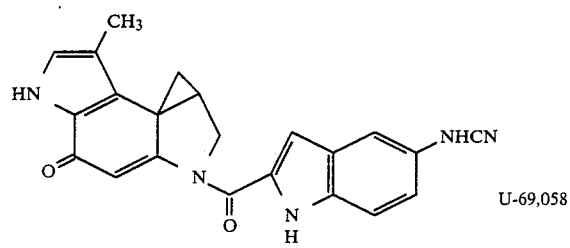
U-69,058
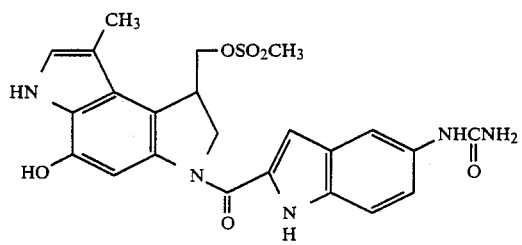
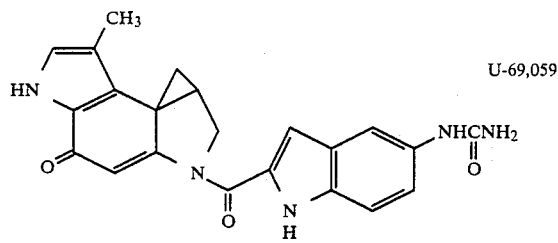
U-69,059
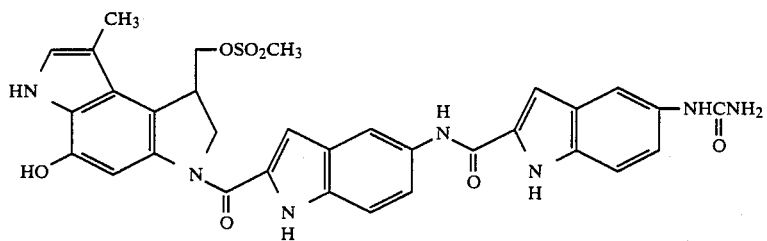

-continued
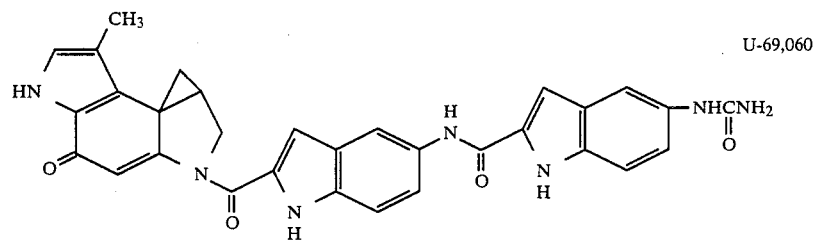
U-69,060
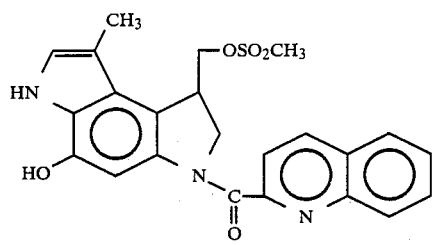
U-69,060 (note: label on image)
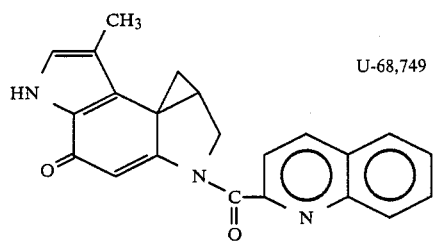
U-68,749
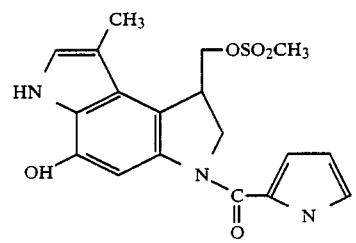
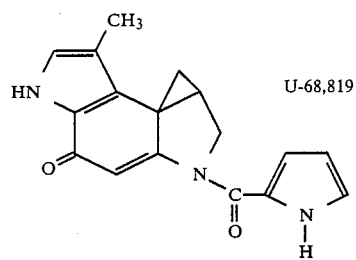
U-68,819
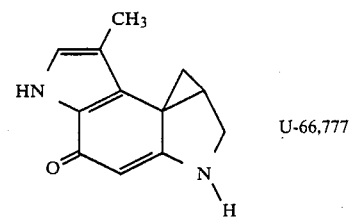
U-66,777

-continued
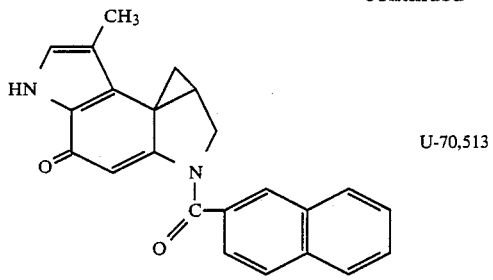
U-70,513
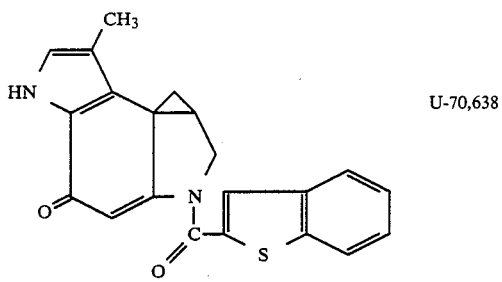
U-70,638
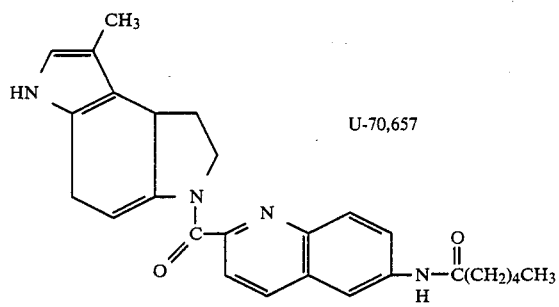
U-70,657
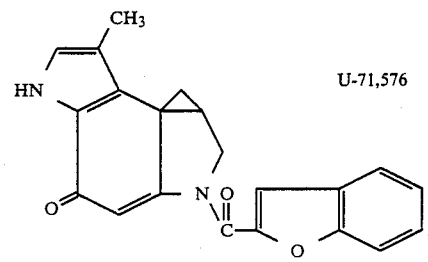
U-71,576
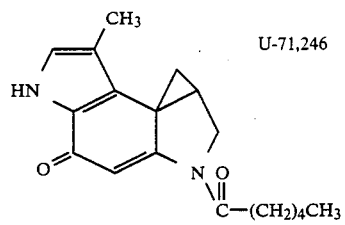
U-71,246
CHART I
Example 1
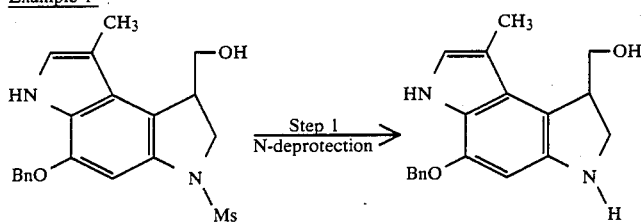
Step 1
N-deprotection -continued
CHART I
Example 2
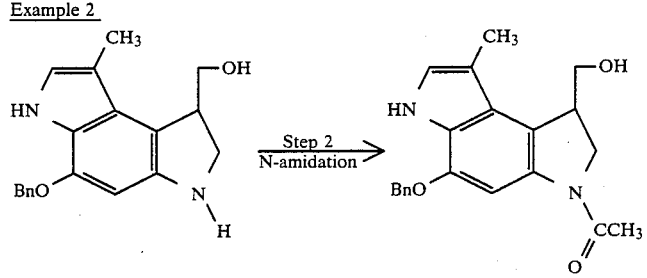
Example 3
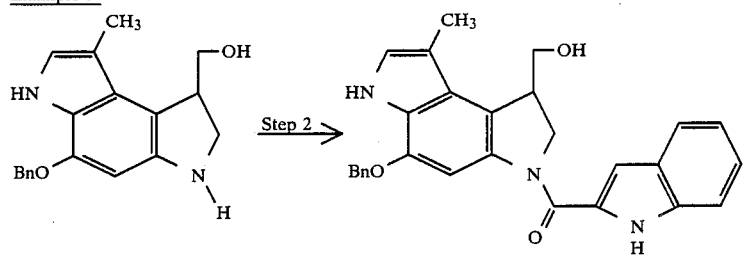
Example 4
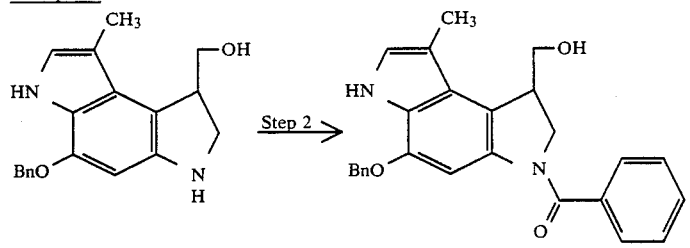
Example 5
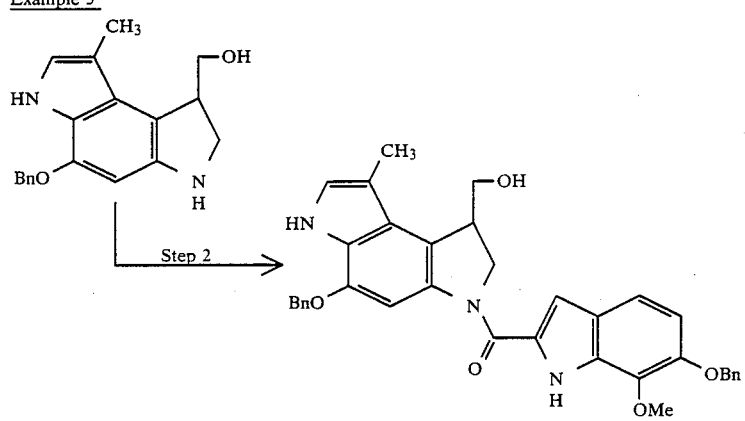
Example 6
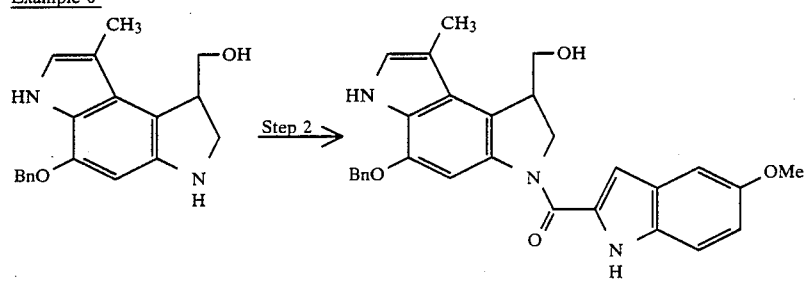
Example 7

-continued
CHART I
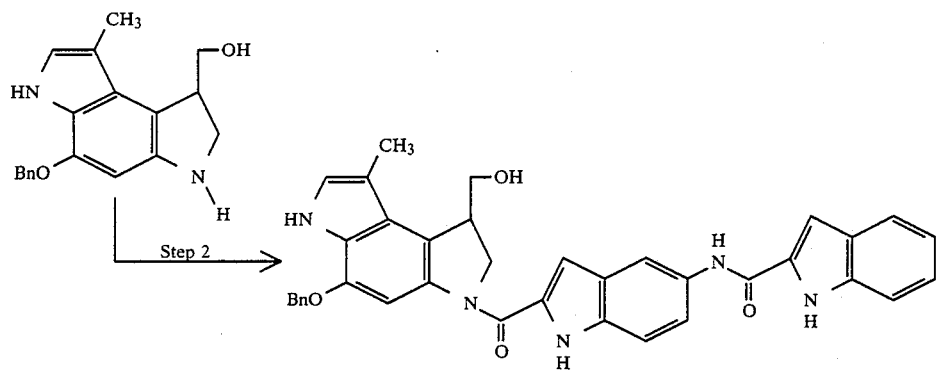
Example 8
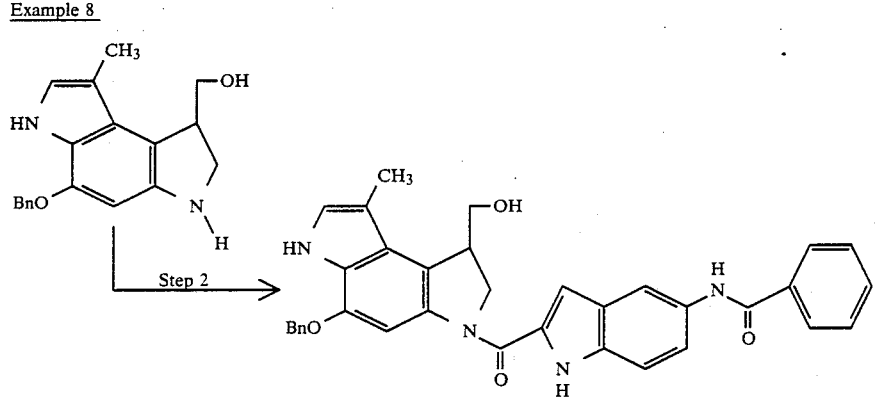
Example 9
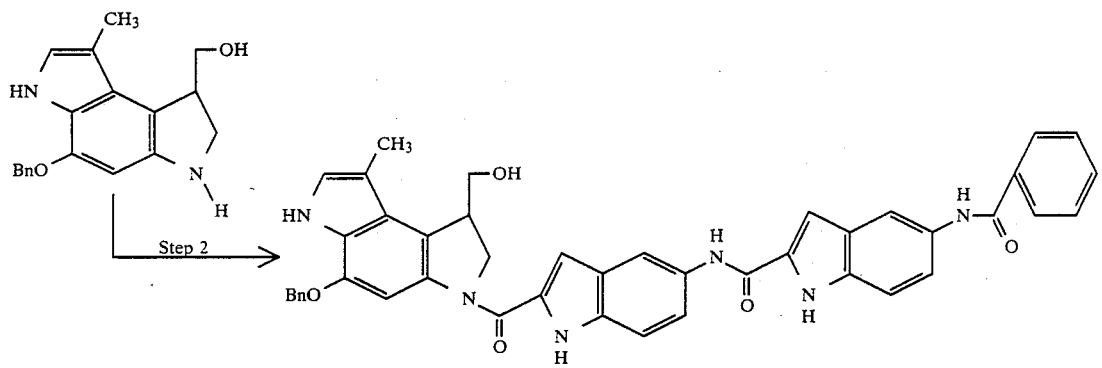
Example 10
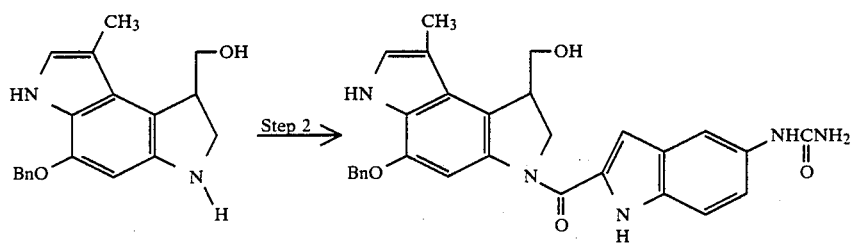
Example 11

-continued
CHART I
Example 12
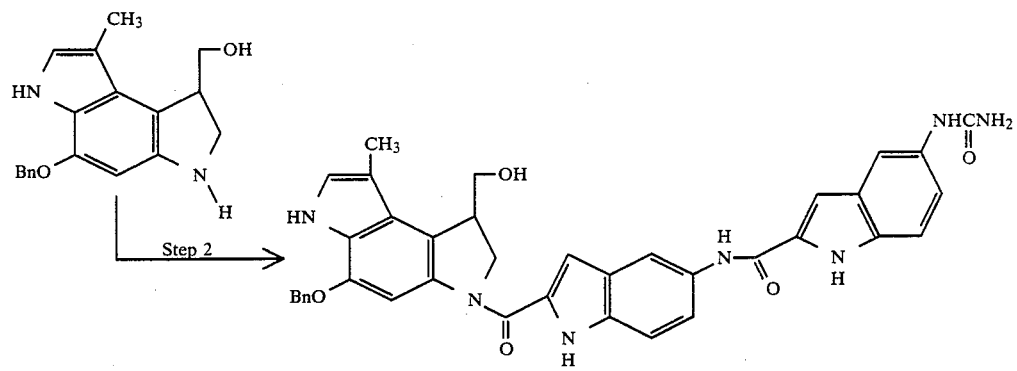
Example 13
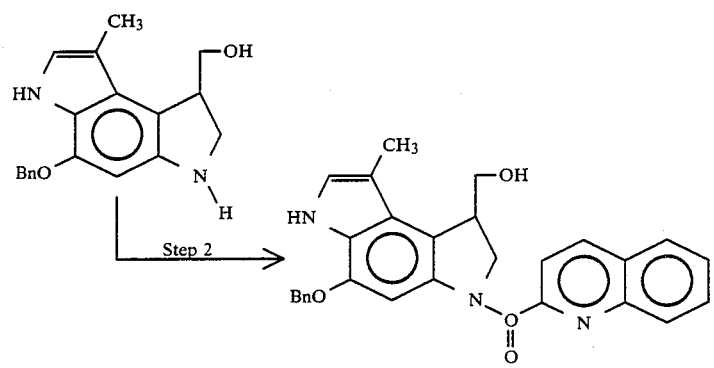
Example 14
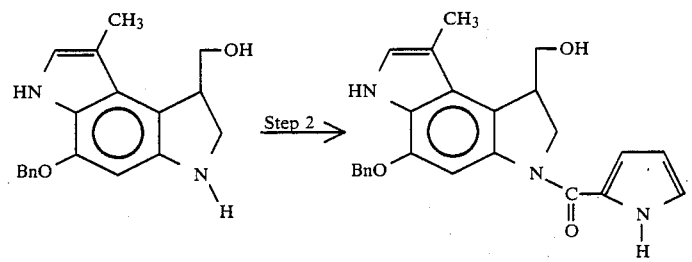
Example 15
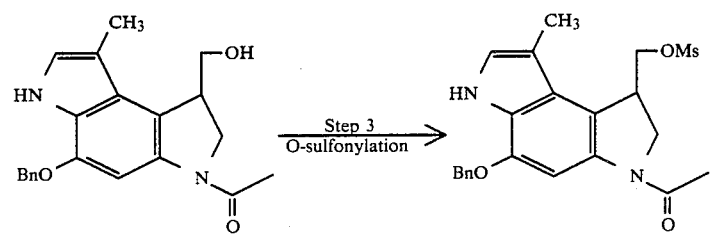

-continued
CHART I
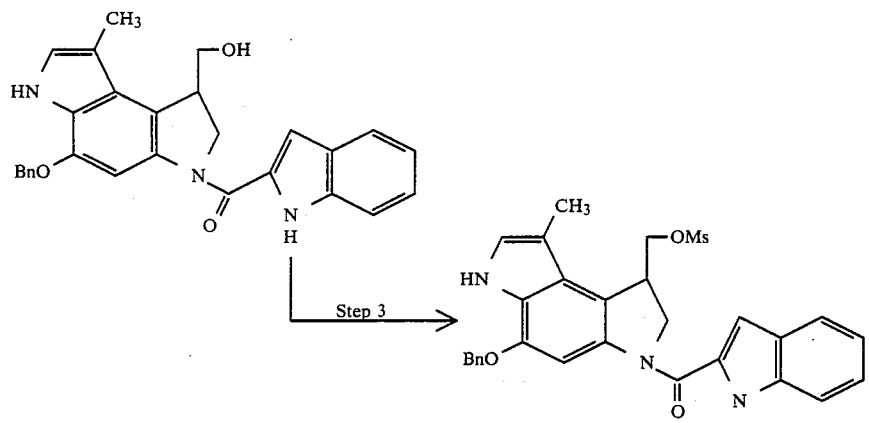
Example 16
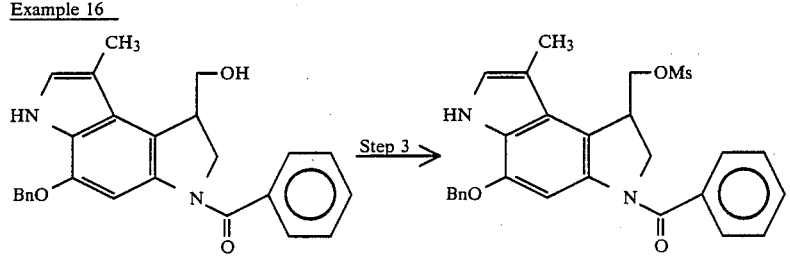
Example 17
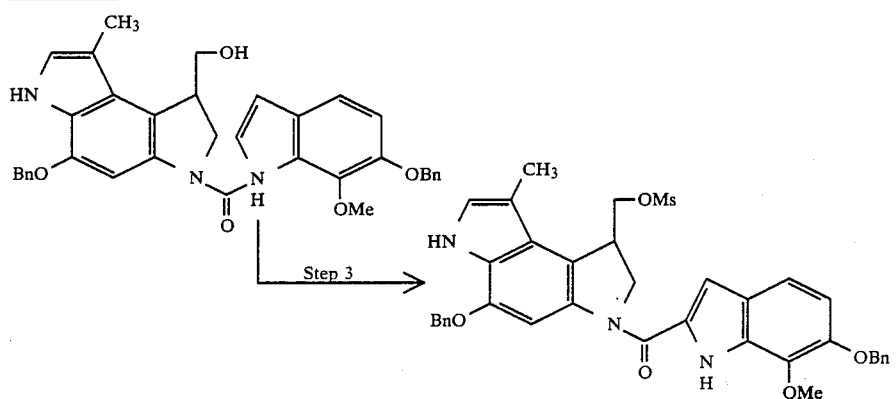
Example 18
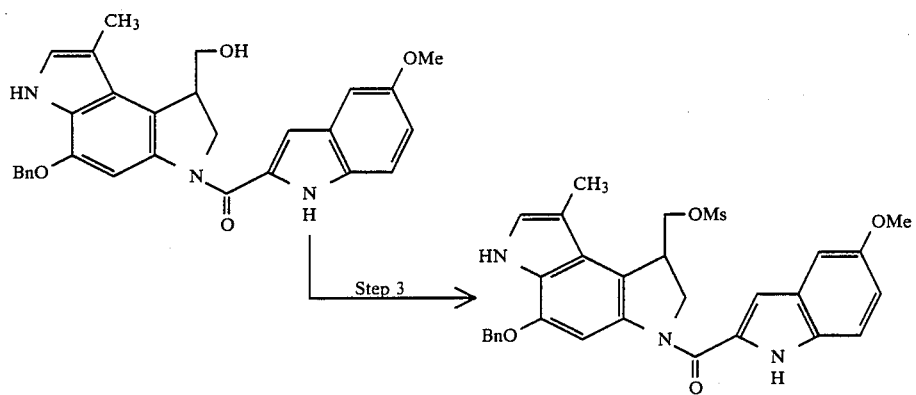
Example 19

4,978,757
-continued
CHART I
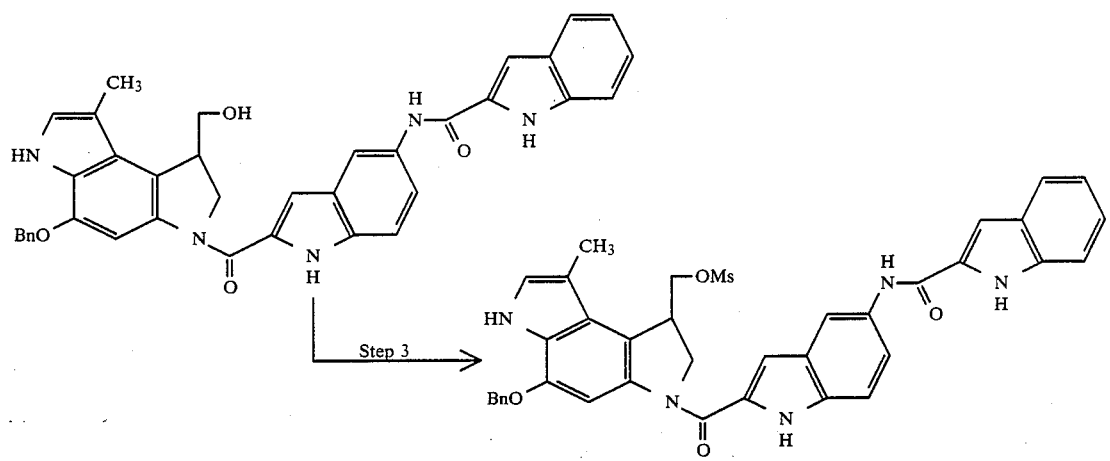
Example 20
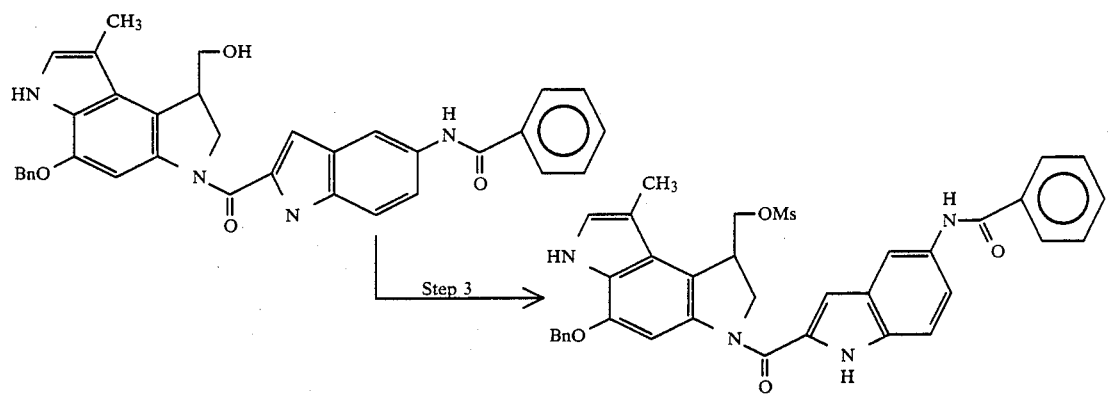
Example 21
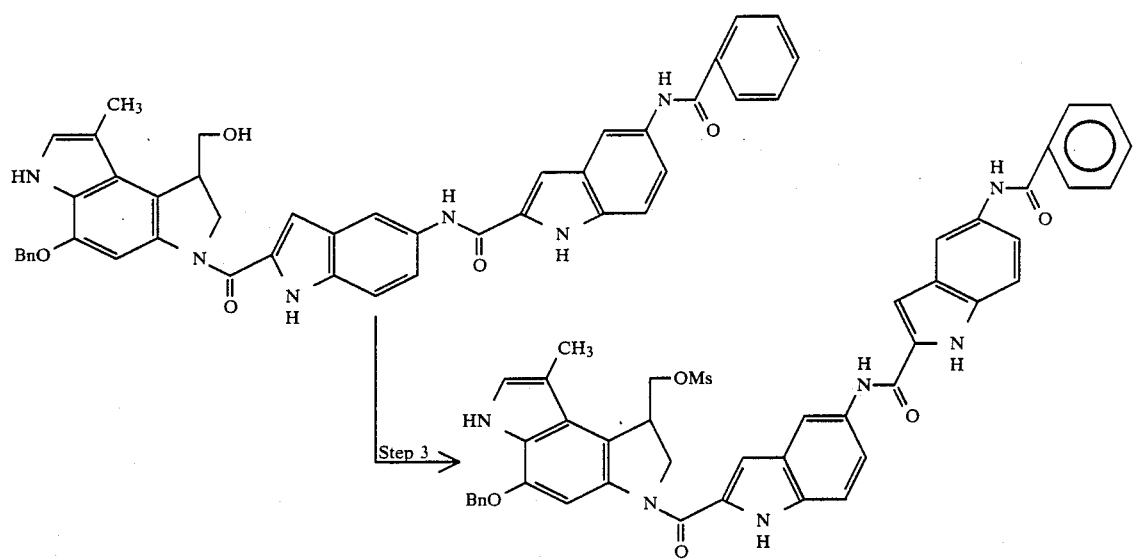
Example 22

-continued
CHART I
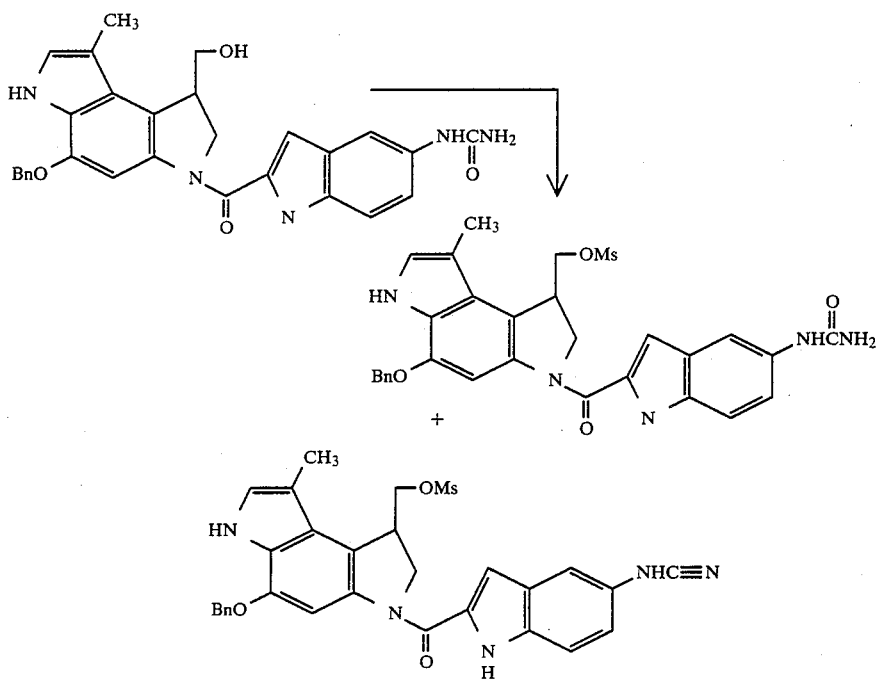
Example 23
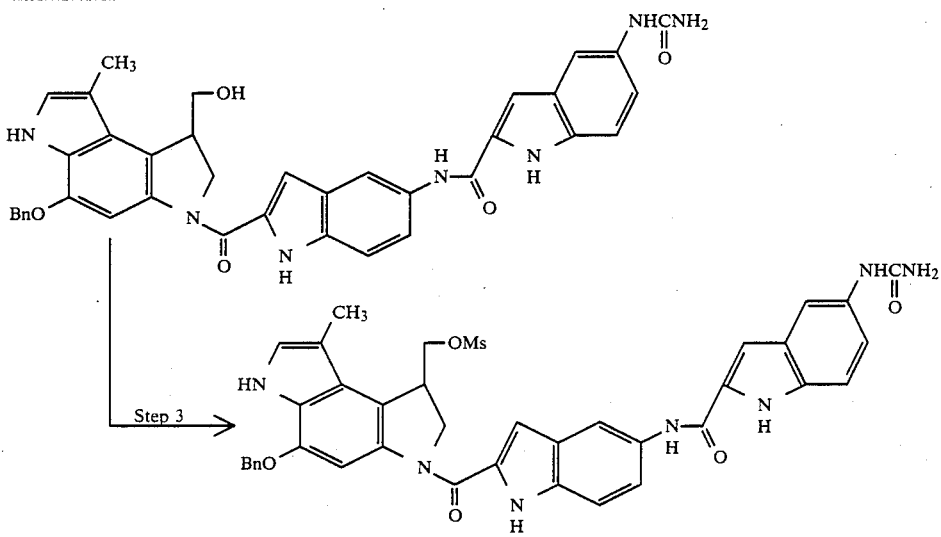
Example 24
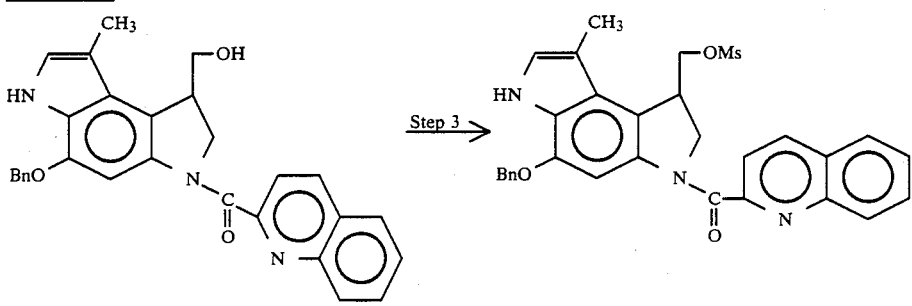
Example 25

4,978,757
-continued
CHART I
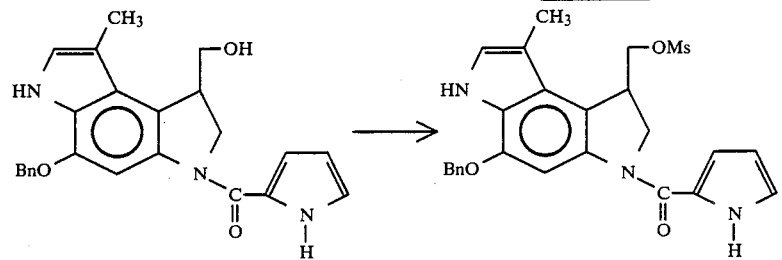
Example 26
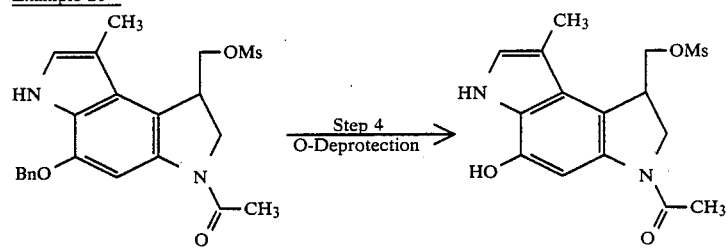
Example 27
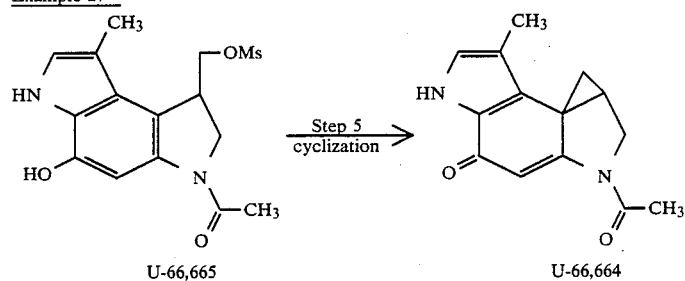
U-66,665 → U-66,664
Example 28
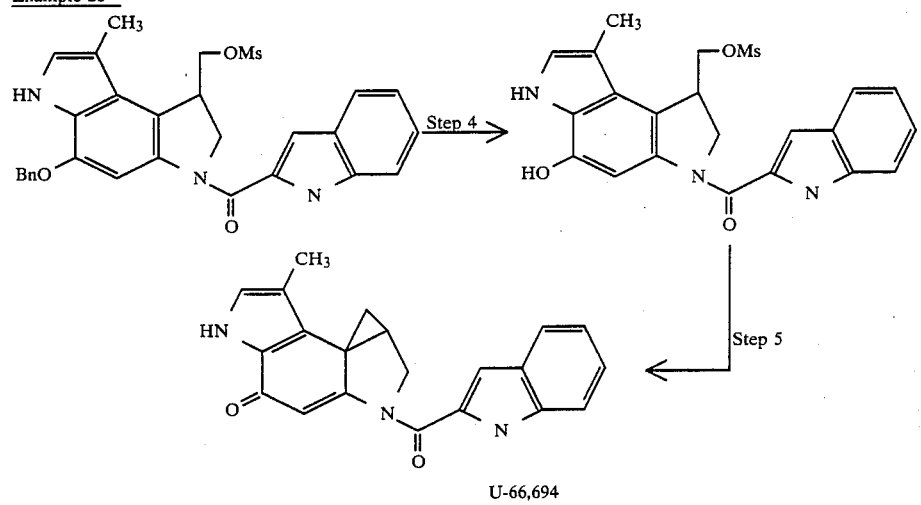
U-66,694
Example 29
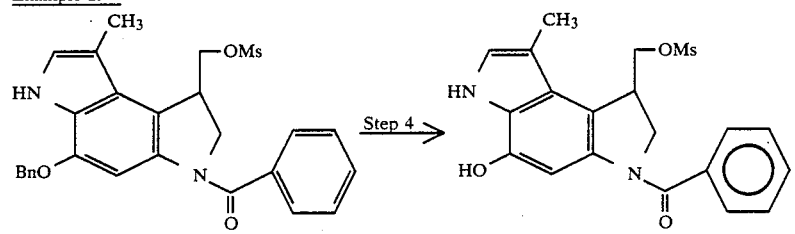

-continued
CHART I
Example 30
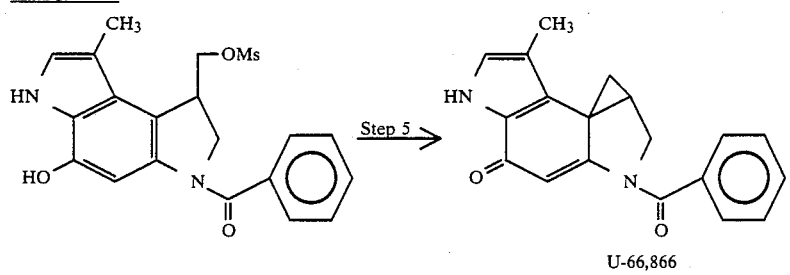
Example 31
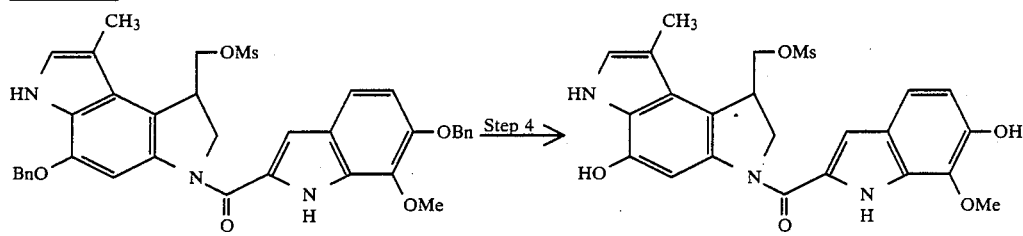
Example 32
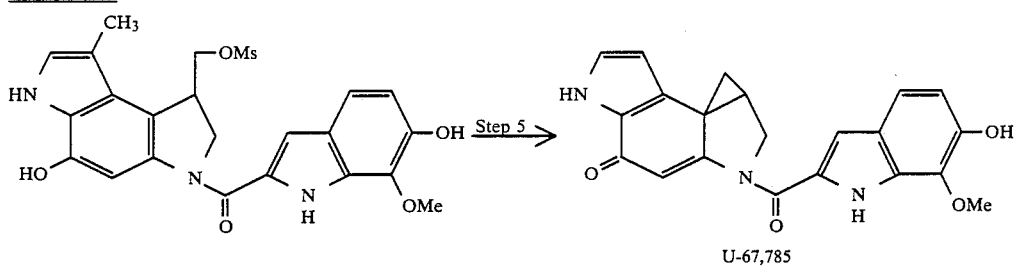
Example 32
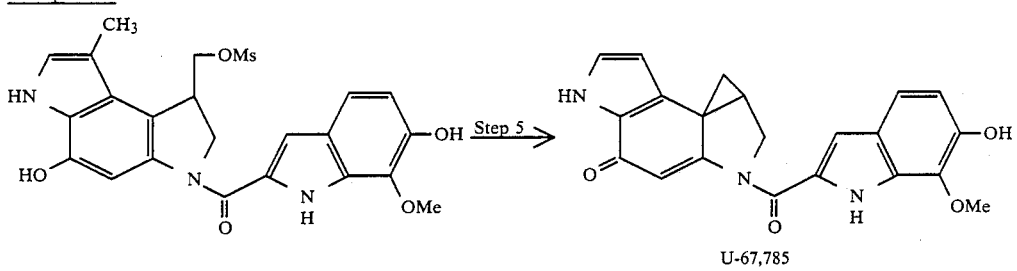
Example 34

-continued
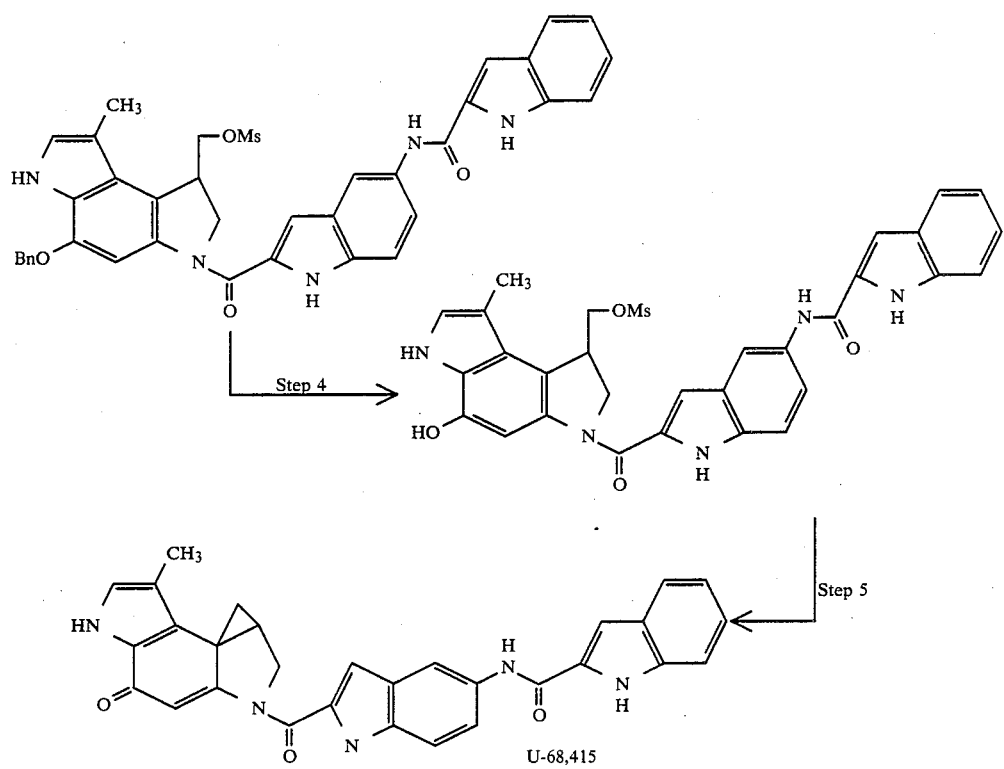
Example 35
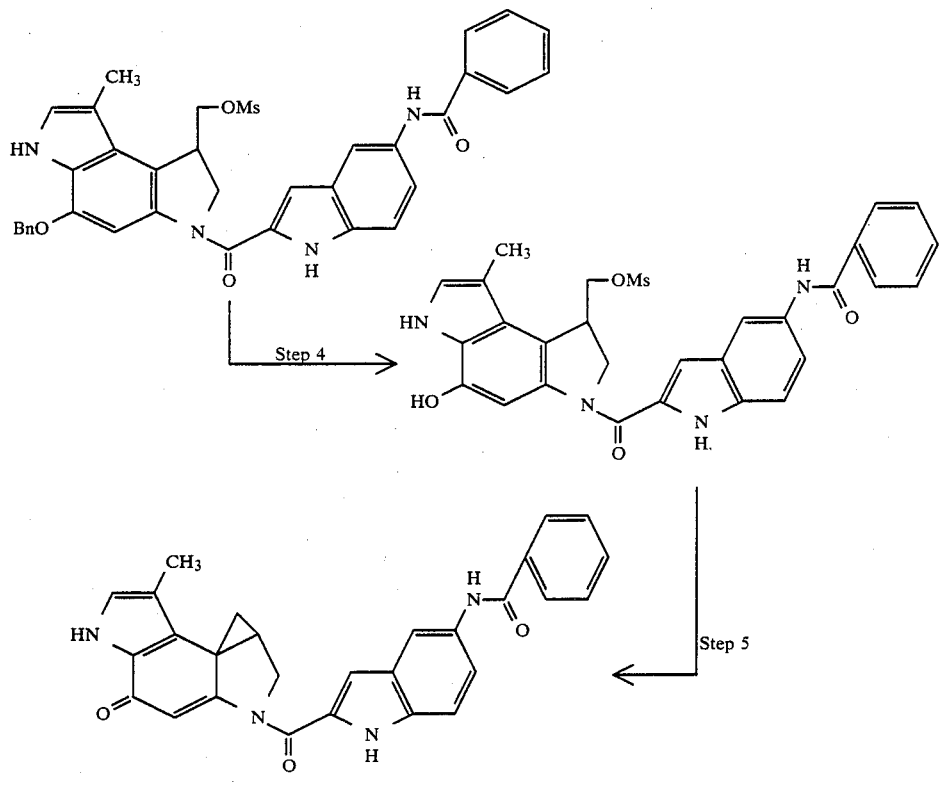
Example 36

-continued
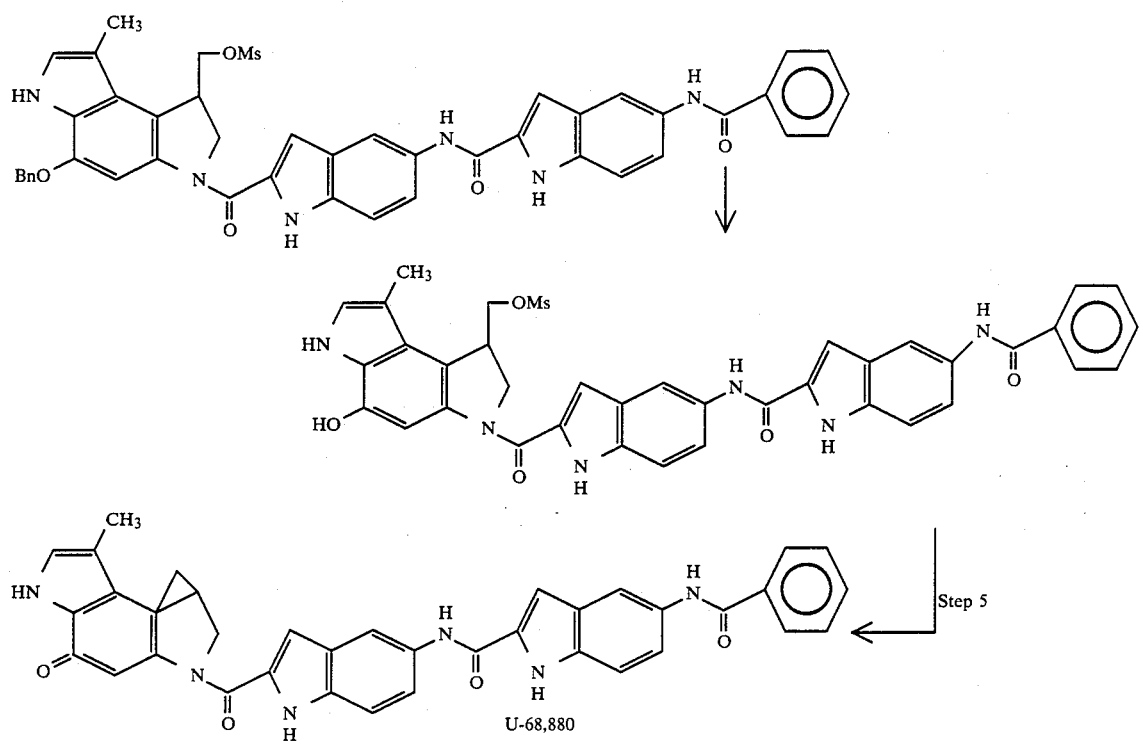
Example 37
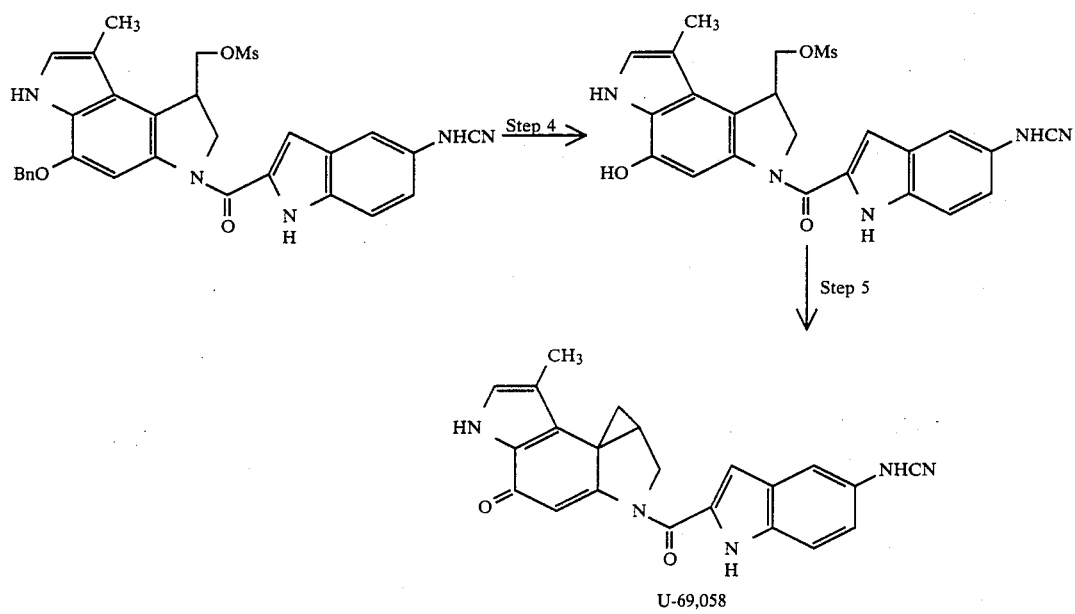
Example 38
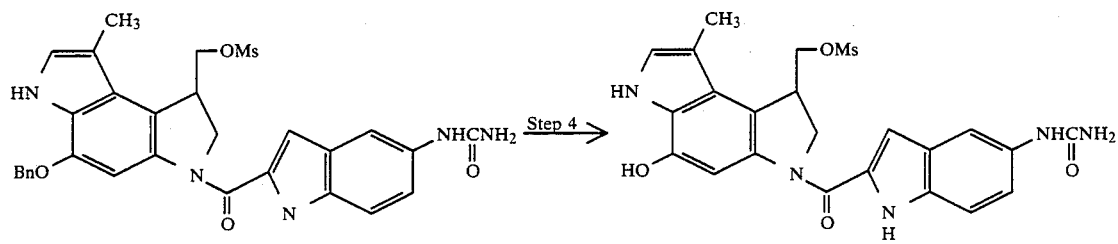

-continued
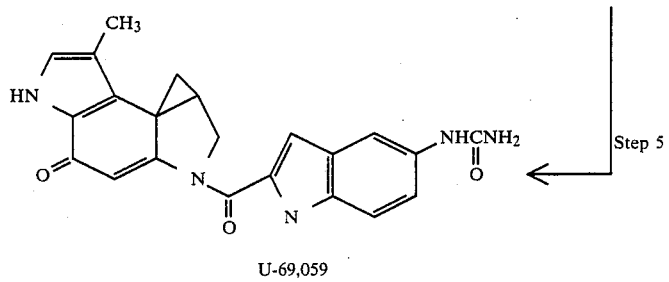
U-69,059
Example 39
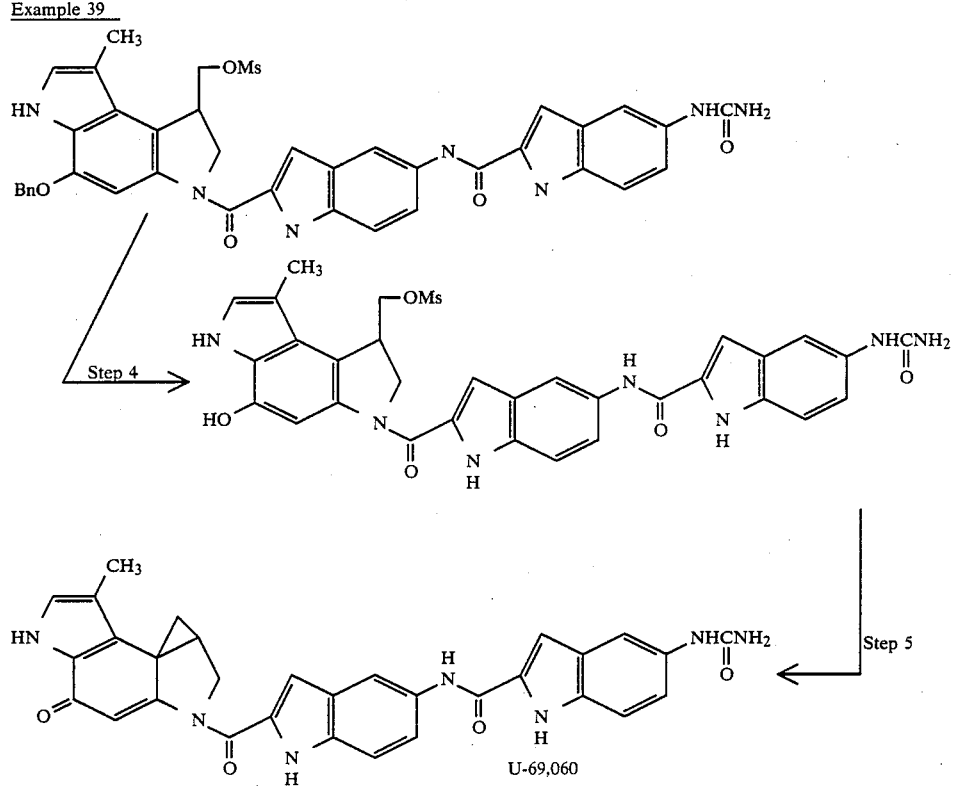
U-69,060
Example 40
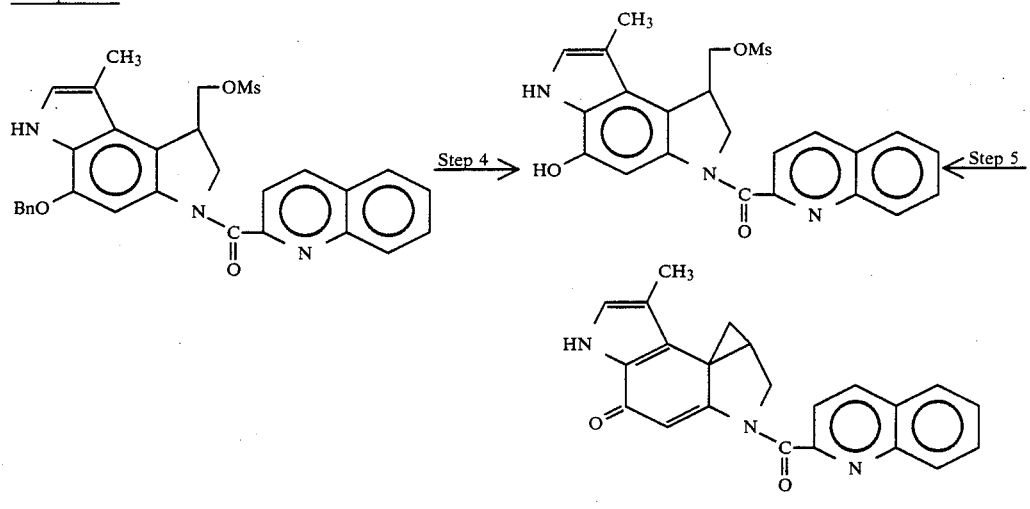
U-68,749
Example 41

4,978,757
-continued
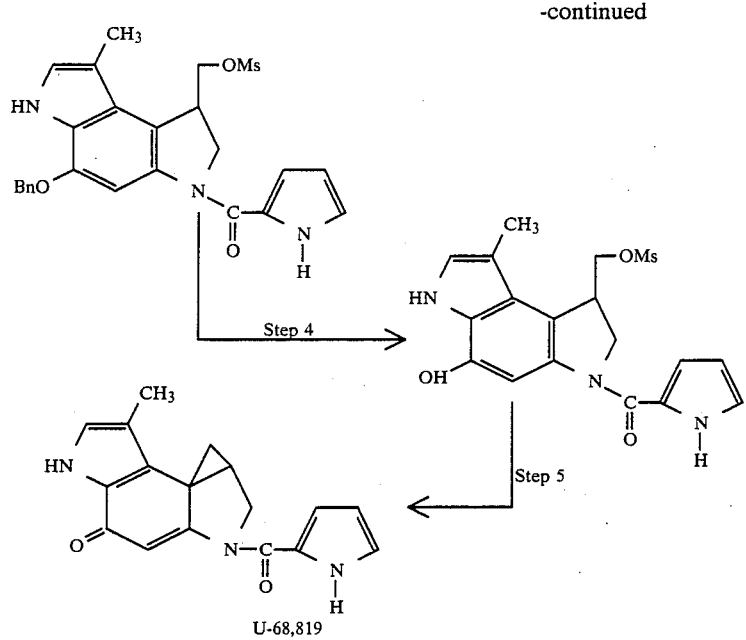
U-68,819
Example 42
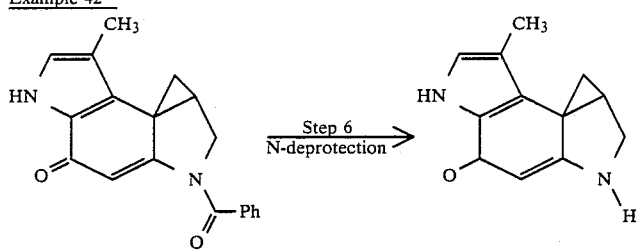
CHART II
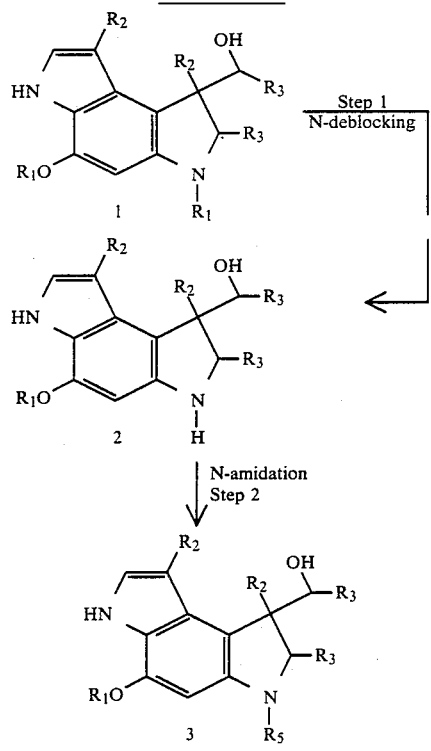
-continued
CHART II
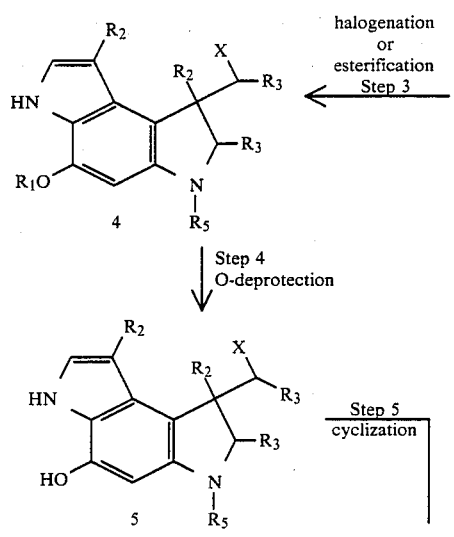

4,978,757
-continued
CHART II
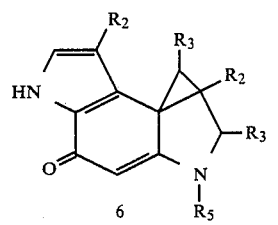
6
N-deprotection
Step 6
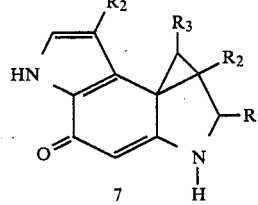
7
CHART III
Step A
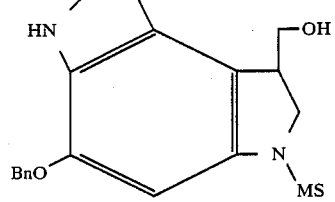
1
(Racemate)
Step 7
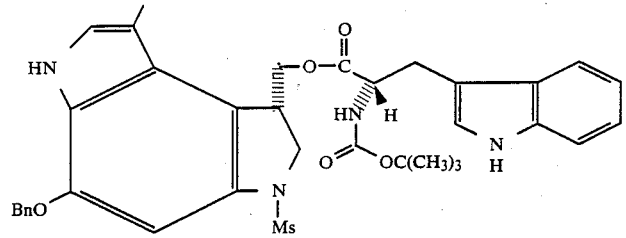
+
(structure)
Step B
(structure)

CHART III
-continued
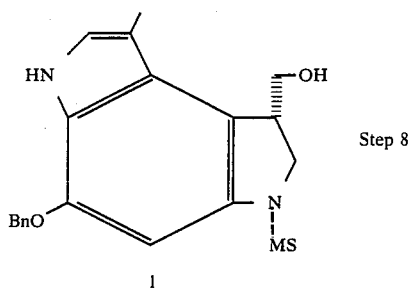
1
(Optically active isomer)
Step 8
Step C
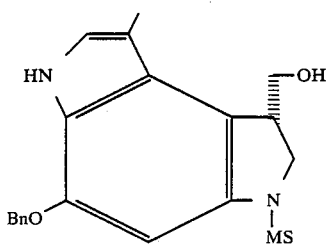
Steps 1–5
as in Examples 1, 7, 19 and 34
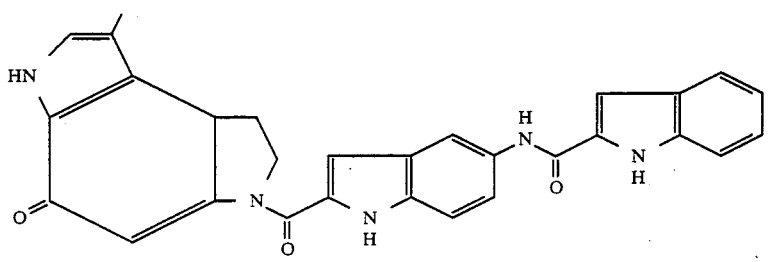
CHART IV
PREPARATION OF U-73,975
Step 1 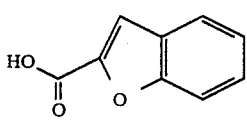
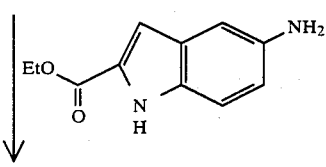

CHART IV -continued
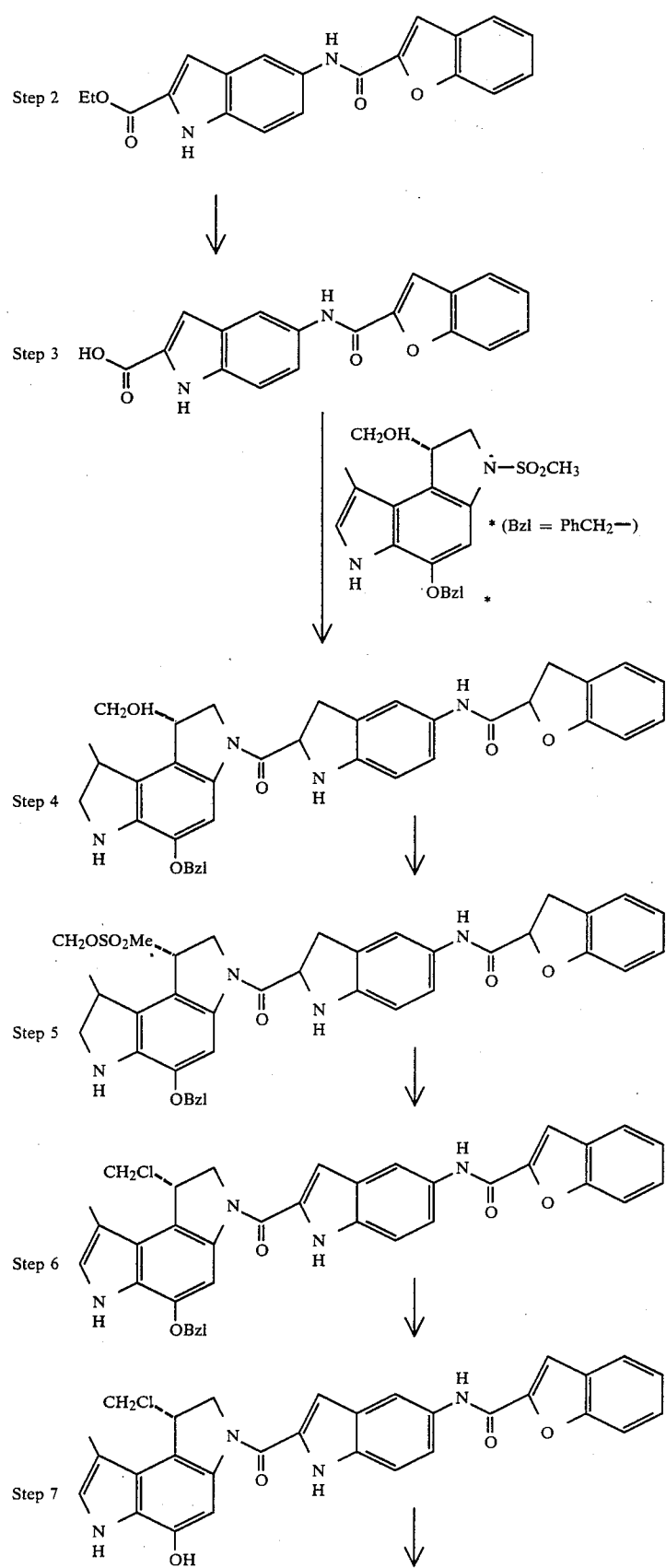

CHART IV
-continued

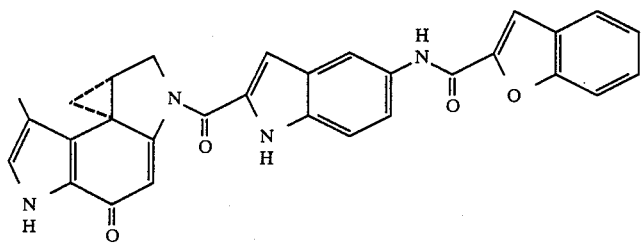

U-73,975

We claim:
1. A compound selected from the group consisting of

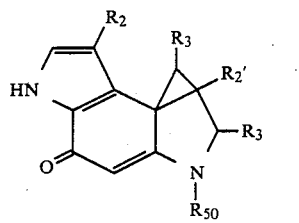 I

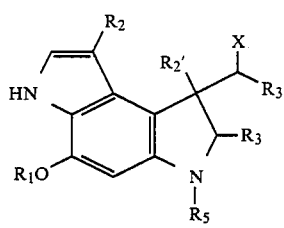 II wherein R₁ is CH₃—, —CH₂Ph, CH₂—CHCH₂—, —CH₂SCH₃, —CH₂OCH₃, —CH₂OCH₂CH₂OCH₃, —CH₂CCl₃, —CH₂CH₂Si(R₂)₃, or H, where Ph is phenyl; R₂ is alkyl($C_1$-$C_5$), phenyl, or H; R₂' is alkyl($C_1$-$C_5$), phenyl, or H; R₂' is alkyl($C_1$-$C_5$), phenyl, or H; R₃ is alkyl($C_1$-$C_5$), phenyl, or H; X is Cl, Br, or I; or OSO₂R₄₀ where R₄₀ is alkyl($C_1$-$C_5$), phenyl, tolyl, bromophenyl, nitrophenyl, or trifluoromethyl; R₅₀ is hydrogen or the same as R₅; R₅ is a carbonyl acyl group selected from the group consisting of

 (i)

where R₆ is H, -alkyl($C_1$-$C_{20}$), —CCl₃, CF₃, or NH₂;

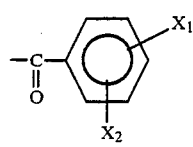 (ii)

where X₁ and/or X₂ is H, CH₃, OH, OCH₃, NO₂, NH₂, NNHAc, NHBz, or halogen;

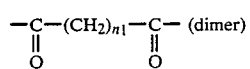 (v)

wherein $n_1$=2-12;

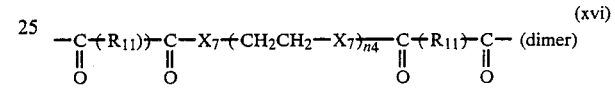 (xvi) (dimer)

where X₇=—O— or —NH—; R₁₁=—CH₂CH₂— or —CH=CH— and $n_4$=1-4.

2. A compound of the formula

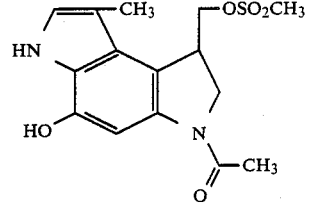

according to claim 1.

3. A compound of the formula

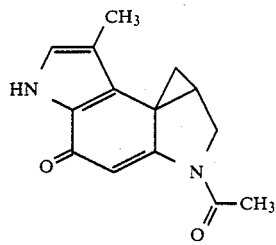

according to claim 1.

4. A compound according to claim 1 selected from the group consisting of

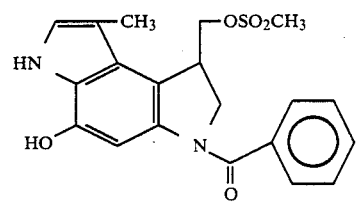 (a)

-continued
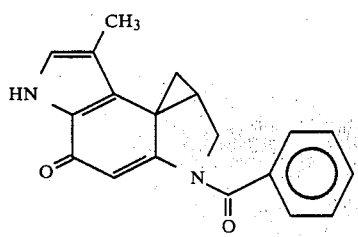
(b)
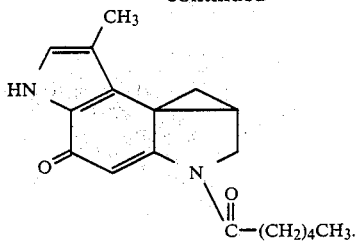
(zb)
* * * * *